(12) United States Patent
Pugh et al.

(10) Patent No.: US 9,671,619 B2
(45) Date of Patent: Jun. 6, 2017

(54) ELECTRONIC OPHTHALMIC LENS WITH EYE GAZE SENSOR

(71) Applicant: Johnson & Johnson Vision Care, Inc., Jacksonville, FL (US)

(72) Inventors: Randall Braxton Pugh, St. Johns, FL (US); Adam Toner, Jacksonville, FL (US); Daniel B. Otts, Fruit Cove, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 56 days.

(21) Appl. No.: 13/780,479

(22) Filed: Feb. 28, 2013

(65) Prior Publication Data
US 2014/0243971 A1 Aug. 28, 2014

(51) Int. Cl.
G02C 7/08 (2006.01)
A61F 2/16 (2006.01)
G02C 7/04 (2006.01)

(52) U.S. Cl.
CPC ............ G02C 7/083 (2013.01); A61F 2/1624 (2013.01); G02C 7/04 (2013.01); G02C 7/081 (2013.01)

(58) Field of Classification Search
CPC ................. G02C 7/04–7/049; A61B 3/113
USPC .................................... 351/159.02
See application file for complete search history.

(56) References Cited

U.S. PATENT DOCUMENTS

| | | | |
|---|---|---|---|
| 7,344,244 B2 | 3/2008 | Goodall | |
| 7,490,936 B2 * | 2/2009 | Blum et al. | 351/159.39 |
| 7,527,375 B2 * | 5/2009 | Blum et al. | 351/159.03 |
| 8,408,706 B2 * | 4/2013 | Yahav | 351/210 |
| 2005/0036109 A1 | 2/2005 | Blum | |
| 2009/0189974 A1 | 7/2009 | Deering | |
| 2009/0195751 A1 | 8/2009 | Hillis | |
| 2009/0279050 A1 | 11/2009 | McGinn | |
| 2010/0204608 A1 * | 8/2010 | Sugio et al. | 600/558 |
| 2010/0331977 A1 | 12/2010 | Schaper, Jr. | |
| 2012/0140167 A1 | 6/2012 | Blum | |
| 2013/0170022 A1 | 7/2013 | Caldeira | |

FOREIGN PATENT DOCUMENTS

| | | |
|---|---|---|
| WO | WO 2010/133317 A9 | 11/2010 |
| WO | WO 2011153112 A2 | 12/2011 |
| WO | WO 2012/061411 A1 | 5/2012 |
| WO | WO 2012/122411 A1 | 9/2012 |

OTHER PUBLICATIONS

European Search Report dated Jun. 12, 2014 for application No. 14157327.9.
Report from the Australian Government dated Apr. 4, 2014 for Application No. 2013204471.

* cited by examiner

*Primary Examiner* — Zachary Wilkes
(74) *Attorney, Agent, or Firm* — Carl J. Evens

(57) ABSTRACT

A gaze direction tracking system for an ophthalmic lens comprising an electronic system is described herein. The gaze direction tracking system is part of an electronic system incorporated into the ophthalmic lens. The electronic system includes one or more batteries or other power sources, power management circuitry, one or more sensors, clock generation circuitry, control algorithms and circuitry, and lens driver circuitry. The gaze direction tracking system is utilized to determine pupil position and use this information to control various aspects of the ophthalmic lens.

25 Claims, 18 Drawing Sheets

ELECTRONIC OPHTHALMIC LENS WITH EYE GAZE SENSOR

BACKGROUND OF THE INVENTION

1. Field of the Invention

The present invention relates to a powered or electronic ophthalmic lens having a sensor and associated hardware and software for detecting eye gaze direction, and more particularly, to a powered or electronic ophthalmic lens comprising a sensor and associated hardware and software for detecting eye gaze direction to change the state of the powered or electronic ophthalmic lens.

2. Discussion of the Related Art

As electronic devices continue to be miniaturized, it is becoming increasingly more likely to create wearable or embeddable microelectronic devices for a variety of uses. Such uses may include monitoring aspects of body chemistry, administering controlled dosages of medications or therapeutic agents via various mechanisms, including automatically, in response to measurements, or in response to external control signals, and augmenting the performance of organs or tissues. Examples of such devices include glucose infusion pumps, pacemakers, defibrillators, ventricular assist devices and neurostimulators. A new, particularly useful field of application is in ophthalmic wearable lenses and contact lenses. For example, a wearable lens may incorporate a lens assembly having an electronically adjustable focus to augment or enhance performance of the eye. In another example, either with or without adjustable focus, a wearable contact lens may incorporate electronic sensors to detect concentrations of particular chemicals in the pre-corneal (tear) film. The use of embedded electronics in a lens assembly introduces a potential requirement for communication with the electronics, for a method of powering and/or re-energizing the electronics, for interconnecting the electronics, for internal and external sensing and/or monitoring, and for control of the electronics and the overall function of the lens.

The human eye has the ability to discern millions of colors, adjust easily to shifting light conditions, and transmit signals or information to the brain at a rate exceeding that of a high-speed internet connection. Lenses, such as contact lenses and intraocular lenses, currently are utilized to correct vision defects such as myopia (nearsightedness), hyperopia (farsightedness), presbyopia and astigmatism. However, properly designed lenses incorporating additional components may be utilized to enhance vision as well as to correct vision defects.

Contact lenses may be utilized to correct myopia, hyperopia, astigmatism as well as other visual acuity defects. Contact lenses may also be utilized to enhance the natural appearance of the wearer's eyes. Contact lenses or "contacts" are simply lenses placed on the anterior surface of the eye. Contact lenses are considered medical devices and may be worn to correct vision and/or for cosmetic or other therapeutic reasons. Contact lenses have been utilized commercially to improve vision since the 1950s. Early contact lenses were made or fabricated from hard materials, were relatively expensive and fragile. In addition, these early contact lenses were fabricated from materials that did not allow sufficient oxygen transmission through the contact lens to the conjunctiva and cornea which potentially could cause a number of adverse clinical effects. Although these contact lenses are still utilized, they are not suitable for all patients due to their poor initial comfort. Later developments in the field gave rise to soft contact lenses, based upon hydrogels, which are extremely popular and widely utilized today. Specifically, silicone hydrogel contact lenses that are available today combine the benefit of silicone, which has extremely high oxygen permeability, with the proven comfort and clinical performance of hydrogels. Essentially, these silicone hydrogel based contact lenses have higher oxygen permeability and are generally more comfortable to wear than the contact lenses made of the earlier hard materials.

Conventional contact lenses are polymeric structures with specific shapes to correct various vision problems as briefly set forth above. To achieve enhanced functionality, various circuits and components have to be integrated into these polymeric structures. For example, control circuits, microprocessors, communication devices, power supplies, sensors, actuators, light-emitting diodes, and miniature antennas may be integrated into contact lenses via custom-built optoelectronic components to not only correct vision, but to enhance vision as well as provide additional functionality as is explained herein. Electronic and/or powered contract lenses may be designed to provide enhanced vision via zoom-in and zoom-out capabilities, or just simply modifying the refractive capabilities of the lenses. Electronic and/or powered contact lenses may be designed to enhance color and resolution, to display textural information, to translate speech into captions in real time, to offer visual cues from a navigation system, and to provide image processing and internet access. The lenses may be designed to allow the wearer to see in low-light conditions. The properly designed electronics and/or arrangement of electronics on lenses may allow for projecting an image onto the retina, for example, without a variable-focus optic lens, provide novelty image displays and even provide wakeup alerts. Alternately, or in addition to any of these functions or similar functions, the contact lenses may incorporate components for the noninvasive monitoring of the wearer's biomarkers and health indicators. For example, sensors built into the lenses may allow a diabetic patient to keep tabs on blood sugar levels by analyzing components of the tear film without the need for drawing blood. In addition, an appropriately configured lens may incorporate sensors for monitoring cholesterol, sodium, and potassium levels, as well as other biological markers. This, coupled with a wireless data transmitter, could allow a physician to have almost immediate access to a patient's blood chemistry without the need for the patient to waste time getting to a laboratory and having blood drawn. In addition, sensors built into the lenses may be utilized to detect light incident on the eye to compensate for ambient light conditions or for use in determining blink patterns.

The proper combination of devices could yield potentially unlimited functionality; however, there are a number of difficulties associated with the incorporation of extra components on a piece of optical-grade polymer. In general, it is difficult to manufacture such components directly on the lens for a number of reasons, as well as mounting and interconnecting planar devices on a non-planar surface. It is also difficult to manufacture to scale. The components to be placed on or in the lens need to be miniaturized and integrated onto just 1.5 square centimeters of a transparent polymer while protecting the components from the liquid environment on the eye. It is also difficult to make a contact lens comfortable and safe for the wearer with the added thickness of additional components.

Given the area and volume constraints of an ophthalmic device such as a contact lens, and the environment in which it is to be utilized, the physical realization of the device must overcome a number of problems, including mounting and interconnecting a number of electronic components on a non-planar surface, the bulk of which comprises optic plastic. Accordingly, there exists a need for providing a mechanically and electrically robust electronic contact lens.

As these are powered lenses, energy or more particularly current consumption, to run the electronics is a concern given battery technology on the scale for an ophthalmic lens. In addition to normal current consumption, powered devices or systems of this nature generally require standby current reserves, precise voltage control and switching capabilities to ensure operation over a potentially wide range of operating parameters, and burst consumption, for example, up to eighteen (18) hours on a single charge, after potentially remaining idle for years. Accordingly, there exists a need for a system that is optimized for low-cost, long-term reliable service, safety and size while providing the required power.

In addition, because of the complexity of the functionality associated with a powered lens and the high level of interaction between all of the components comprising a powered lens, there is a need to coordinate and control the overall operation of the electronics and optics comprising a powered ophthalmic lens. Accordingly, there is a need for a system to control the operation of all of the other components that is safe, low-cost, and reliable, has a low rate of power consumption and is scalable for incorporation into an ophthalmic lens.

Powered or electronic ophthalmic lenses may have to account for certain unique physiological functions from the individual utilizing the powered or electronic ophthalmic lens. More specifically, powered lenses may have to account for blinking, including the number of blinks in a given time period, the duration of a blink, the time between blinks and any number of possible blink patterns, for example, if the individual is dosing off. Blink detection may also be utilized to provide certain functionality, for example, blinking may be utilized as a means to control one or more aspects of a powered ophthalmic lens. Additionally, external factors, such as changes in light intensity levels, and the amount of visible light that a person's eyelid blocks out, have to be accounted for when determining blinks. For example, if a room has an illumination level between fifty-four (54) and one hundred sixty-one (161) lux, a photosensor should be sensitive enough to detect light intensity changes that occur when a person blinks.

Ambient light sensors or photosensors are utilized in many systems and products, for example, on televisions to adjust brightness according to the room light, on lights to switch on at dusk, and on phones to adjust the screen brightness. However, these currently utilized sensor systems are not small enough and/or do not have low enough power consumption for incorporation into contact lenses.

It is also important to note that different types of blink detectors may be implemented with computer vision systems directed at one's eye(s), for example, a camera digitized to a computer. Software running on the computer can recognize visual patterns such as the eye open and closed. These systems may be utilized in ophthalmic clinical settings for diagnostic purposes and studies. Unlike the above described detectors and systems, these systems are intended for off eye use and to look at rather than look away from the eye. Although these systems are not small enough to be incorporated into contact lenses, the software utilized may be similar to the software that would work in conjunction with powered contact lenses. Either system may incorporate software implementations of artificial neural networks that learn from input and adjust their output accordingly. Alternately, non-biology based software implementations incorporating statistics, other adaptive algorithms, and/or signal processing may be utilized to create smart systems.

Accordingly, there exists a need for a means and method for detecting certain physiological functions, such as a blink, and utilizing them to activate and/or control an electronic or powered ophthalmic lens according to the type of blink sequence detected by a sensor. The sensor being utilized having to be sized and configured for use in a contact lens.

Alternately, pupil convergence rather than or in addition to blinking may be utilized to control the functionality of a contact lens in certain circumstances. When an individual focuses on a near object, for example when reading, his/her pupils converge to fix the gaze of both eyes on the same location. This phenomena is based on the geometry of the system, a triangle being formed by the two eyes and the area of focus, and attention being brought to a specific, nearby object. This effect is used in the design of spectacles, stereoscopes, and related instruments to ensure clear and comfortable vision when gazing at nearby objects. This effect may also be monitored in a clinical setting, for example by recording a user's pupil positions by observing them with a camera and performing pattern recognition functions. Pupil convergence could also be detected by a similar camera and detection system implemented in spectacle lenses.

Because of the correlation between pupil convergence and focusing on near objects, pupil convergence may be used to trigger actions in an electronic ophthalmic lens, for example, changing the power of a variable power optic to allow an individual with presbyopia to focus on near objects. In addition to pupil convergence, the direction of gaze of an individual may be tracked and this tracking information may be utilized to control a powered ophthalmic lens.

Accordingly, there exists a need for a means and method for detecting certain physiological functions, such as pupil convergence and gaze direction, and utilizing them to activate and/or control an electronic or powered ophthalmic lens according to pupil convergence detected by a sensor. The sensor being utilized is preferably sized and configured for use in a powered or electronic contact lens.

SUMMARY OF THE INVENTION

The electronic ophthalmic lens with gaze direction sensor in accordance with the present invention overcomes the limitations associated with the prior art as briefly described above. The sensor detects and tracks pupil position as a convenient method for changing the state of an electronic ophthalmic device, for example, changing focus for a presbyopic user. The sensor is integrated into a contact lens instead of requiring bulky external observation equipment or spectacle lenses. The sensor system has the necessary low power consumption and small size to be implemented in a contact lens. The system has the necessary signal conditioning and sample rate for pleasant, natural use. The system has the necessary signal conditioning and communication methods to avoid false positive and false negative convergence detection.

In accordance with one aspect, the present invention is directed to a powered ophthalmic lens. The powered ophthalmic lens comprises a contact lens including an optic zone and a peripheral zone, and an eye gaze tracking system incorporated into the peripheral zone of the contact lens, the eye gaze tracking system including a sensor to determine and track eye position, a system controller cooperatively associated with the sensor, the system controller configured to determine and track gaze direction in spatial coordinates based on information from the sensor output a control signal, and at least one actuator configured to receive the output control signal and implement a predetermined function.

In accordance with another aspect, the present invention is directed to a powered ophthalmic lens. The powered ophthalmic lens comprises a contact lens, and an eye gaze tracking system incorporated into the contact lens, the eye gaze tracking system including a sensor to determine and track eye position, a system controller cooperatively associated with the sensor, the system controller configured to determine and track gaze direction in spatial coordinates based on information from the sensor output a control signal, and at least one actuator configured to receive the output control signal and implement a predetermined function.

In accordance with yet another aspect, the present invention is directed to a powered ophthalmic lens. The powered ophthalmic lens comprises an intraocular lens, and an eye gaze tracking system incorporated into the intraocular lens, the eye gaze tracking system including a sensor to determine and track eye position, a system controller cooperatively associated with the sensor, the system controller configured to determine and track gaze direction in spatial coordinates based on information from the sensor output a control signal, and at least one actuator configured to receive the output control signal and implement a predetermined function.

Eye tracking is the process of determining either or both where an individual is looking, point of gaze, or the motion of an eye relative to the head. An individual's gaze direction is determined by the orientation of the head and the orientation of the eyes. More specifically, the orientation of an individual's head determines the overall direction of the gaze while the orientation of the individual's eyes determines the exact gaze direction which in turn is limited by the orientation of the head. Information of where an individual is gazing provides the ability to determine the individual's focus of attention and this information may be utilized in any number of disciplines or application, including cognitive science, psychology, human-computer interaction, marketing research and medical research. For example, eye gaze direction may be utilized as a direct input into a controller or computer to control another action. In other words, simple eye movements may be utilized to control the actions of other devices, including highly complex functions. Simple eye movements may be utilized in a manner similar to "swipes" which have become common in touch-screen and smartphone applications, for example, swiping to unlock a device, change applications, change pages, zoom in or out and the like. Eye gaze tracking systems are presently utilized to restore communication and functionality to those who are paralyzed, for example, using eye movements to operate computers. Eye tracking or gaze tracking may also be utilized in any number of commercial applications, for example, what individuals are paying attention to when they are watching television, browsing websites and the like. The data collected from this tracking may be statistically analyzed to provide evidence of specific visual patterns. Accordingly, information garnered from detecting eye or pupil movement may be utilized in a wide range applications.

There are a number of currently available devices for tracking eye movement, including video-based eye trackers, search coils and arrangements for generating electrooculograms. Search coils or inductive sensors are devices which measure the variations of the surrounding magnetic fields. Essentially, a number of coils may be imbedded into a contact lens type device and the polarity and amplitude of the current generated in the coils varies with the direction and angular displacement of the eye. An electrooculogram is generated by a device for the detection of eye movement and eye position based on the difference in electrical potential between electrodes placed on either side of the eye. All of these devices are not suitable for use with a wearable, comfortable electronic ophthalmic lens or powered contact lens. Therefore, in accordance with another exemplary embodiment, the present invention is directed to a powered contact lens comprising a gaze sensor incorporated directly into the contact lens.

The present invention more generally relates to a powered contact lens comprising an electronic system, which performs any number of functions, including actuating a variable-focus optic if included. The electronic system includes one or more batteries or other power sources, power management circuitry, one or more sensors, clock generation circuitry, control algorithms and circuitry, and lens driver circuitry.

Control of a powered ophthalmic lens may be accomplished through a manually operated external device that communicates with the lens wirelessly, such as a hand-held remote unit. Alternately, control of the powered ophthalmic lens may be accomplished via feedback or control signals directly from the wearer. For example, sensors built into the lens may detect blinks and/or blink patterns. Based upon the pattern or sequence of blinks, the powered ophthalmic lens may change state, for example, its refractive power in order to either focus on a near object or a distant object. Alternately or in addition to, pupil convergence and/or gaze direction may be utilized to change the state of a powered application lens.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Figure 1:
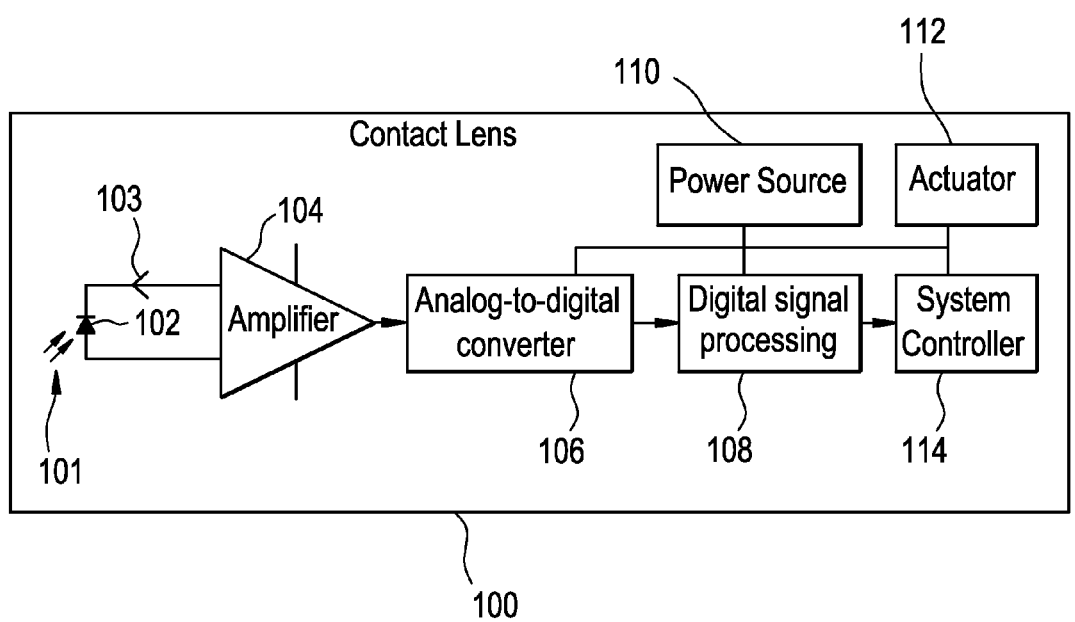
FIG. 1 illustrates an exemplary contact lens comprising a blink detection system in accordance with some embodiments of the present invention.

Conventional contact lenses are polymeric structures with specific shapes to correct various vision problems as briefly set forth above. To achieve enhanced functionality, various circuits and components may be integrated into these polymeric structures. For example, control circuits, microprocessors, communication devices, power supplies, sensors, actuators, light-emitting diodes, and miniature antennas may be integrated into contact lenses via custom-built optoelectronic components to not only correct vision, but to enhance vision as well as provide additional functionality as is explained herein. Electronic and/or powered contact lenses may be designed to provide enhanced vision via zoom-in and zoom-out capabilities, or just simply modifying the refractive capabilities of the lenses. Electronic and/or powered contact lenses may be designed to enhance color and resolution, to display textural information, to translate speech into captions in real time, to offer visual cues from a navigation system, and to provide image processing and internet access. The lenses may be designed to allow the wearer to see in low light conditions. The properly designed electronics and/or arrangement of electronics on lenses may allow for projecting an image onto the retina, for example, without a variable focus optic lens, provide novelty image displays and even provide wakeup alerts. Alternately, or in addition to any of these functions or similar functions, the contact lenses may incorporate components for the noninvasive monitoring of the wearer's biomarkers and health indicators. For example, sensors built into the lenses may allow a diabetic patient to keep tabs on blood sugar levels by analyzing components of the tear film without the need for drawing blood. In addition, an appropriately configured lens may incorporate sensors for monitoring cholesterol, sodium, and potassium levels, as well as other biological markers. This coupled with a wireless data transmitter could allow a physician to have almost immediate access to a patient's blood chemistry without the need for the patient to waste time getting to a laboratory and having blood drawn. In addition, sensors built into the lenses may be utilized to detect light incident on the eye to compensate for ambient light conditions or for use in determining blink patterns.

The powered or electronic contact lens of the present invention comprises the necessary elements to correct and/or enhance the vision of patients with one or more of the above described vision defects or otherwise perform a useful ophthalmic function. In addition, the electronic contact lens may be utilized simply to enhance normal vision or provide a wide variety of functionality as described above. The electronic contact lens may comprise a variable focus optic lens, an assembled front optic embedded into a contact lens or just simply embedding electronics without a lens for any suitable functionality. The electronic lens of the present invention may be incorporated into any number of contact lenses as described above. In addition, intraocular lenses may also incorporate the various components and functionality described herein. However, for ease of explanation, the disclosure will focus on an electronic contact lens to correct vision defects intended for single-use daily disposability.

The present invention may be employed in a powered ophthalmic lens or powered contact lens comprising an electronic system, which actuates a variable-focus optic or any other device or devices configured to implement any number of numerous functions that may be performed. The electronic system includes one or more batteries or other power sources, power management circuitry, one or more sensors, clock generation circuitry, control algorithms and circuitry, and lens driver circuitry. The complexity of these components may vary depending on the required or desired functionality of the lens.

Control of an electronic or a powered ophthalmic lens may be accomplished through a manually operated external device that communicates with the lens, such as a hand-held remote unit. For example, a fob may wirelessly communicate with the powered lens based upon manual input from the wearer. Alternately, control of the powered ophthalmic lens may be accomplished via feedback or control signals directly from the wearer. For example, sensors built into the lens may detect blinks and/or blink patterns. Based upon the pattern or sequence of blinks, the powered ophthalmic lens may change state, for example, its refractive power in order to either focus on a near object or a distant object.

Alternately, blink detection in a powered or electronic ophthalmic lens may be used for other various uses where there is interaction between the user and the electronic contact lens, such as activating another electronic device, or sending a command to another electronic device. For example, blink detection in an ophthalmic lens may be used in conjunction with a camera on a computer wherein the camera keeps track of where the eye(s) moves on the computer screen, and when the user executes a blink sequence that it detected, it causes the mouse pointer to perform a command, such as double-clicking on an item, highlighting an item, or selecting a menu item.

A blink detection algorithm is a component of the system controller which detects characteristics of blinks, for example, is the lid open or closed, the duration of the blink, the inter-blink duration, and the number of blinks in a given time period. The algorithm in accordance with the present invention relies on sampling light incident on the eye at a certain sample rate. Pre-determined blink patterns are stored and compared to the recent history of incident light samples. When patterns match, the blink detection algorithm may trigger activity in the system controller, for example, to activate the lens driver to change the refractive power of the lens.

Blinking is the rapid closing and opening of the eyelids and is an essential function of the eye. Blinking protects the eye from foreign objects, for example, individuals blink when objects unexpectedly appear in proximity to the eye. Blinking provides lubrication over the anterior surface of the eye by spreading tears. Blinking also serves to remove contaminants and/or irritants from the eye. Normally, blinking is done automatically, but external stimuli may contribute as in the case with irritants. However, blinking may also be purposeful, for example, for individuals who are unable to communicate verbally or with gestures can blink once for yes and twice for no. The blink detection algorithm and system of the present invention utilizes blinking patterns that cannot be confused with normal blinking response. In other words, if blinking is to be utilized as a means for controlling an action, then the particular pattern selected for a given action cannot occur at random; otherwise inadvertent actions may occur. As blink speed may be affected by a number of factors, including fatigue, eye injury, medication and disease, blinking patterns for control purposes preferably account for these and any other variables that affect blinking. The average length of involuntary blinks is in the range of about one hundred (100) to four hundred (400) milliseconds. Average adult men and women blink at a rate of ten (10) involuntary blinks per minute, and the average time between involuntary blinks is about 0.3 to seventy (70) seconds.

An exemplary embodiment of the blink detection algorithm may be summarized in the following steps.

1. Define an intentional "blink sequence" that a user will execute for positive blink detection.

2. Sample the incoming light level at a rate consistent with detecting the blink sequence and rejecting involuntary blinks.

3. Compare the history of sampled light levels to the expected "blink sequence," as defined by a blink template of values.

4. Optionally implement a blink "mask" sequence to indicate portions of the template to be ignored during comparisons, e.g. near transitions. This may allow for a user to deviate from a desired "blink sequence," such as a plus or minus one (1) error window, wherein one or more of lens activation, control, and focus change can occur. Additionally, this may allow for variation in the user's timing of the blink sequence.

An exemplary blink sequence may be defined as follows:
1. blink (closed) for 0.5 s
2. open for 0.5 s
3. blink (closed) for 0.5 s At a one hundred (100) ms sample rate, a twenty (20) sample blink template is given by
blink_template=[1,1,1, 0,0,0,0,0, 1,1,1,1, 0,0,0,0,0, 1,1].

The blink mask is defined to mask out the samples just after a transition (0 to mask out or ignore samples), and is given by
blink_mask=[1,1,1, 0,1,1,1,1, 0,1,1,1,1, 0,1,1,1,1, 0,1].

Optionally, a wider transition region may be masked out to allow for more timing uncertainty, and is given by
blink_mask=[1,1,0, 0,1,1,1,0, 0,1,1,1,0, 0,1,1,1,0, 0,1].

Alternate patterns may be implemented, e.g. single long blink, in this case a 1.5 s blink with a 24-sample template, given by
blink_template=[1,1,1,1,0,0, 0,0,0,0,0,0, 0,0,0,0,0,0, 0,1,1,1,1,1].

It is important to note that the above example is for illustrative purposes and does not represent a specific set of data.

Detection may be implemented by logically comparing the history of samples against the template and mask. The logical operation is to exclusive-OR (XOR) the template and the sample history sequence, on a bitwise basis, and then verify that all unmasked history bits match the template. For example, as illustrated in the blink mask samples above, in each place of the sequence of a blink mask that the value is logic 1, a blink has to match the blink mask template in that place of the sequence. However, in each place of the sequence of a blink mask that the value is logic 0, it is not necessary that a blink matches the blink mask template in that place of the sequence. For example, the following Boolean algorithm equation, as coded in MATLAB®, may be utilized.

matched=not (blink_mask)|not (xor (blink_template, test_sample)), wherein test_sample is the sample history. The matched value is a sequence with the same length as the blink template, sample history and blink_mask. If the matched sequence is all logic 1's, then a good match has occurred. Breaking it down, not (xor (blink_template, test_sample)) gives a logic 0 for each mismatch and a logic 1 for each match. Logic oring with the inverted mask forces each location in the matched sequence to a logic 1 where the mask is a logic 0. Accordingly, the more places in a blink mask template where the value is specified as logic 0, the greater the margin of error in relation to a person's blinks is allowed. MATLAB® is a high level language and implementation for numerical computation, visualization and programming and is a product of MathWorks, Natick, Mass. It is also important to note that the greater the number of logic 0's in the blink mask template, the greater the potential for false positive matched to expected or intended blink patterns. It should be appreciated that a variety of expected or intended blink patterns may be programmed into a device with one or more active at a time. More specifically, multiple expected or intended blink patterns may be utilized for the same purpose or functionality, or to implement different or alternate functionality. For example, one blink pattern may be utilized to cause the lens to zoom in or out on an intended object while another blink pattern may be utilized to cause another device, for example, a pump, on the lens to deliver a dose of a therapeutic agent.

FIG. 1 illustrates, in block diagram form, a contact lens 100, comprising an electronic blink detector system, in accordance with an exemplary embodiment of the present invention. In this exemplary embodiment, the electronic blink detector system may comprise a photosensor 102, an amplifier 104, an analog-to-digital converter or ADC 106, a digital signal processor 108, a power source 110, an actuator 112, and a system controller 114.

When the contact lens 100 is placed onto the front surface of a user's eye the electronic circuitry of the blink detector system may be utilized to implement the blink detection algorithm of the present invention. The photosensor 102, as well as the other circuitry, is configured to detect blinks and/or various blink patterns produced by the user's eye.

In this exemplary embodiment, the photosensor 102 may be embedded into the contact lens 100 and receives ambient light 101, converting incident photons into electrons and thereby causing a current, indicated by arrow 103, to flow into the amplifier 104. The photosensor or photodetector 102 may comprise any suitable device. In one exemplary embodiment, the photosensor 102 comprises a photodiode. In a preferred exemplary embodiment, the photodiode is implemented in a complimentary metal-oxide semiconductor (CMOS process technology) to increase integration ability and reduce the overall size of the photosensor 102 and the other circuitry. The current 103 is proportional to the incident light level and decreases substantially when the photodetector 102 is covered by an eyelid. The amplifier 104 creates an output proportional to the input, with gain, and may function as a transimpedance amplifier which converts input current into output voltage. The amplifier 104 may amplify a signal to a useable level for the remainder of the system, such as giving the signal enough voltage and power to be acquired by the ADC 106. For example, the amplifier may be necessary to drive subsequent blocks since the output of the photosensor 102 may be quite small and may be used in low-light environments. The amplifier 104 may be implemented as a variable-gain amplifier, the gain of which may be adjusted by the system controller 114, in a feedback arrangement, to maximize the dynamic range of the system. In addition to providing gain, the amplifier 104 may include other analog signal conditioning circuitry, such as filtering and other circuitry appropriate to the photosensor 102 and amplifier 104 outputs. The amplifier 104 may comprise any suitable device for amplifying and conditioning the signal output by the photosensor 102. For example, the amplifier 104 may simply comprise a single operational amplifier or a more complicated circuit comprising one or more operational amplifiers. As set forth above, the photosensor 102 and the amplifier 104 are configured to detect and isolate blink sequences based upon the incident light intensity received through the eye and convert the input current into a digital signal usable ultimately by the system controller 114. The system controller 114 is preferably preprogrammed or preconfigured to recognize various blink sequences and/or blink patterns in various light intensity level conditions and provide an appropriate output signal to the actuator 112. The system controller 114 also comprises associated memory.

In this exemplary embodiment, the ADC 106 may be used to convert a continuous, analog signal output from the amplifier 104 into a sampled, digital signal appropriate for further signal processing. For example, the ADC 106 may convert an analog signal output from the amplifier 104 into a digital signal that may be useable by subsequent or downstream circuits, such as a digital signal processing system or microprocessor 108. A digital signal processing system or digital signal processor 108 may be utilized for digital signal processing, including one or more of filtering, processing, detecting, and otherwise manipulating/processing sampled data to permit incident light detection for downstream use. The digital signal processor 108 may be preprogrammed with the blink sequences and/or blink patterns described above. The digital signal processor 108 also comprises associated memory. The digital signal processor 108 may be implemented utilizing analog circuitry, digital circuitry, software, or a combination thereof. In the illustrate exemplary embodiment, it is implemented in digital circuitry. The ADC 106 along with the associated amplifier 104 and digital signal processor 108 are activated at a suitable rate in agreement with the sampling rate previously described, for example every one hundred (100) ms.

A power source 110 supplies power for numerous components comprising the blink detection system. The power may be supplied from a battery, energy harvester, or other suitable means as is known to one of ordinary skill in the art. Essentially, any type of power source 110 may be utilized to provide reliable power for all other components of the system. A blink sequence may be utilized to change the state of the system and/or the system controller. Furthermore, the system controller 114 may control other aspects of a powered contact lens depending on input from the digital signal processor 108, for example, changing the focus or refractive power of an electronically controlled lens through the actuator 112.

Figure 2:
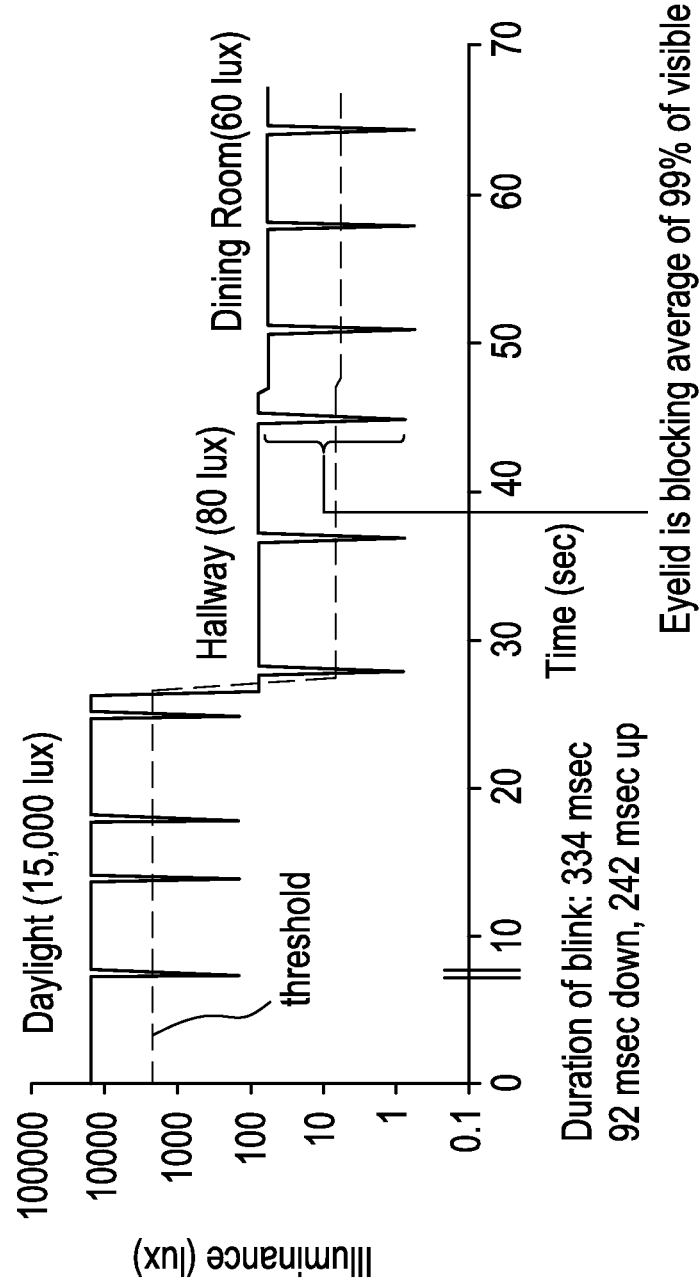
FIG. 2 illustrates a graphical representation of light incident on the surface of the eye versus time, illustrating a possible involuntary blink pattern recorded at various light intensity levels versus time and a usable threshold level based on some point between the maximum and minimum light intensity levels in accordance with the present invention.

The system controller 114 uses the signal from the photosensor chain; namely, the photosensor 102, the amplifier 104, the ADC 106 and the digital signal processing system 108, to compare sampled light levels to blink activation patterns. Referring to FIG. 2, a graphical representation of blink pattern samples recorded at various light intensity levels versus time and a usable threshold level is illustrated. Accordingly, accounting for various factors may mitigate and/or prevent error in detecting blinks when sampling light incident on the eye, such as accounting for changes in light intensity levels in different places and/or while performing various activities. Additionally, when sampling light incident on the eye, accounting for the effects that changes in ambient light intensity may have on the eye and eyelid may also mitigate and/or prevent error in detecting blinks, such as how much visible light an eyelid blocks when it is closed in low-intensity light levels and in high-intensity light levels. In other words, in order to prevent erroneous blinking patterns from being utilized to control, the level of ambient light is preferably accounted for as is explained in greater detail below.

For example, in a study, it has been found that the eyelid on average blocks approximately ninety-nine (99) percent of visible light, but at lower wavelengths less light tends to be transmitted through the eyelid, blocking out approximately 99.6 percent of visible light. At longer wavelengths, toward the infrared portion of the spectrum, the eyelid may block only thirty (30) percent of the incident light. What is important to note; however, is that light at different frequencies, wavelengths and intensities may be transmitted through the eyelids with different efficiencies. For example, when looking at a bright light source, an individual may see red light with his or her eyelids closed. There may also be variations in how much visible light an eyelid blocks based upon an individual, such as an individual's skin pigmentation. As is illustrated in FIG. 2, data samples of blink patterns across various lighting levels are simulated over the course of a seventy (70) second time interval wherein the visible light intensity levels transmitted through the eye are recorded during the course of the simulation, and a usable threshold value is illustrated. The threshold is set at a value in between the peak-to-peak value of the visible light intensity recorded for the sample blink patterns over the course of the simulation at varying light intensity levels. Having the ability to preprogram blink patterns while tracking an average light level over time and adjusting a threshold may be critical to being able to detect when an individual is blinking, as opposed to when an individual is not blinking and/or there is just a change in light intensity level in a certain area.

Referring now again to FIG. 1, in further alternate exemplary embodiments, the system controller 114 may receive input from sources including one or more of a blink detector, eye muscle sensors, and a fob control. By way of generalization, it may be obvious to one skilled in the art that the method of activating and/or controlling the system controller 114 may require the use of one or more activation methods. For example, an electronic or powered contact lens may be programmable specific to an individual user, such as programming a lens to recognize both of an individual's blink patterns and an individual's ciliary muscle signals when performing various actions, for example, focusing on an object far away, or focusing on an object that is near. In some exemplary embodiments, using more than one method to activate an electronic contact lens, such as blink detection and ciliary muscle signal detection, may give the ability for each method to be crosschecked with another before activation of the contact lens occurs. An advantage of crosschecking may include mitigation of false positives, such as minimizing the chance of unintentionally triggering a lens to activate. In one exemplary embodiment, the crosschecking may involve a voting scheme, wherein a certain number of conditions are met prior to any action taking place.

The actuator 112 may comprise any suitable device for implementing a specific action based upon a received command signal. For example, if a blink activation pattern is matched compared to a sampled light level as described above, the system controller 114 may enable the actuator 112, such as a variable-optic electronic or powered lens. The actuator 112 may comprise an electrical device, a mechanical device, a magnetic device, or any combination thereof. The actuator 112 receives a signal from the system controller 114 in addition to power from the power source 110 and produces some action based on the signal from the system controller 114. For example, if the system controller 114 signal is indicative of the wearer trying to focus on a near object, the actuator 112 may be utilized to change the refractive power of the electronic ophthalmic lens, for example, via a dynamic multi-liquid optic zone. In an alternate exemplary embodiment, the system controller 114 may output a signal indicating that a therapeutic agent should be delivered to the eye(s). In this exemplary embodiment, the actuator 112 may comprise a pump and reservoir, for example, a microelectromechanical system (MEMS) pump. As set forth above, the powered lens of the present invention may provide various functionality; accordingly, one or more actuators may be variously configured to implement the functionality.

Figure 3:
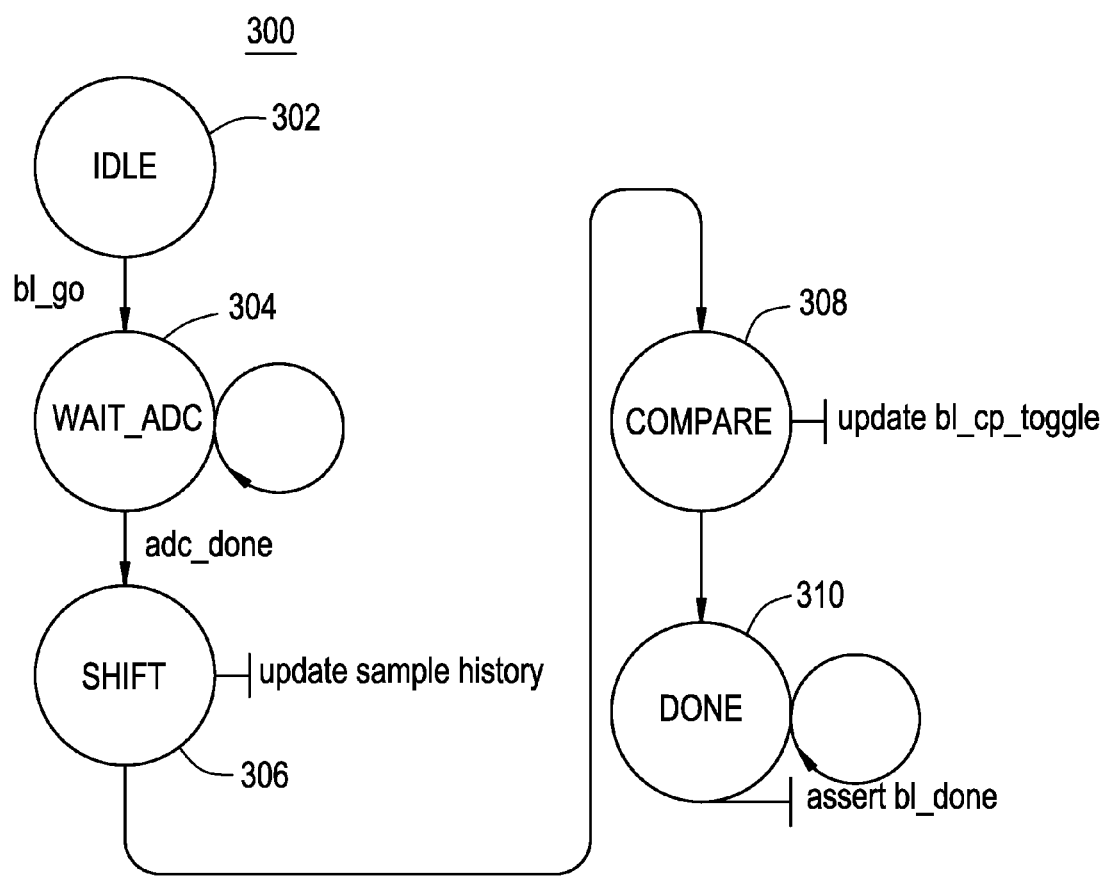
FIG. 3 is an exemplary state transition diagram of a blink detection system in accordance with the present invention.

FIG. 3 illustrates a state transition diagram 300 for an exemplary blink detection system in accordance with the blink detection algorithm of the present invention. The system starts in an IDLE state 302 waiting for an enable signal bl_go to be asserted. When the enable bl_go signal is asserted, for example, by an oscillator and control circuit which pulses bl_go at a one hundred (100) ms rate commensurate with the blink sampling rate, the state machine then transitions to a WAIT_ADC state 304 in which an ADC is enabled to convert a received light level to a digital value. The ADC asserts an adc_done signal to indicate its operations are complete, and the system or state machine transitions to a SHIFT state 306. In the SHIFT state 306 the system pushes the most recently received ADC output value onto a shift register to hold the history of blink samples. In some exemplary embodiments, the ADC output value is first compared to a threshold value to provide a single bit (1 or 0) for the sample value, in order to minimize storage requirements. The system or state machine then transitions to a COMPARE state 308 in which the values in the sample history shift register are compared to one or more blink sequence templates and masks as described above. If a match is detected, one or more output signals may be asserted, such as one to toggle the state of the lens driver, bl_cp_toggle, or any other functionality to be performed by the powered ophthalmic lens. The system or state machine then transitions to the DONE state 310 and asserts a bl_done signal to indicate its operations are complete.

Figure 4:
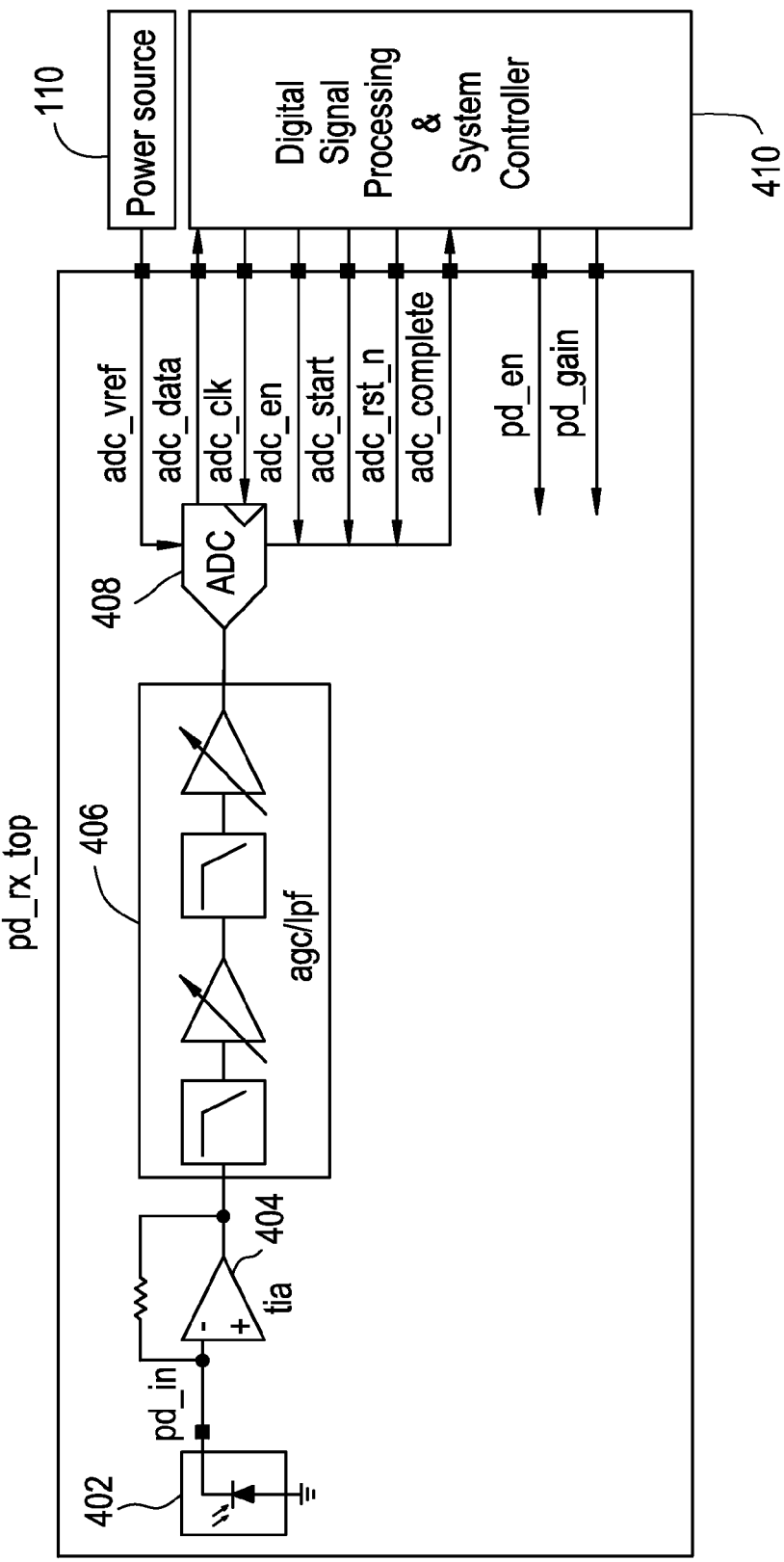
FIG. 4 is a diagrammatic representation of a photodetection path utilized to detect and sample received light signals in accordance with the present invention.

FIG. 4 illustrates an exemplary photosensor or photodetector signal path pd_rx_top that may be used to detect and sample received light levels. The signal path pd_rx_top may comprise a photodiode 402, a transimpedance amplifier 404, an automatic gain and low pass filtering stage 406 (AGC/LPF), and an ADC 408. The adc_vref signal is input to the ADC 408 from the power source 110 (see FIG. 1) or alternately it may be provided from a dedicated circuit inside the analog-to-digital converter 408. The output from the ADC 408, adc_data, is transmitted to the digital signal processing and system controller block 108/114 (see FIG. 1). Although illustrated in FIG. 1 as individual blocks 108 and 114, for ease of explanation, the digital signal processing and system controller are preferably implemented on a single block 410. The enable signal, adc_en, the start signal, adc_start, and the reset signal, adc_rst_n are received from the digital signal processing and system controller 410 while the complete signal, adc_complete, is transmitted thereto. The clock signal, adc_clk, may be received from a clock source external to the signal path, pd_rx_top, or from the digital signal processing and system controller 410. It is important to note that the adc_clk signal and the system clock may be running at different frequencies. It is also important to note that any number of different ADCs may be utilized in accordance with the present invention which may have different interface and control signals but which perform a similar function of providing a sampled, digital representation of the output of the analog portion of the photosensor signal path. The photodetect enable, pd_en, and the photodetect gain, pd_gain, are received from the digital signal processing and system controller 410.

Figure 5:
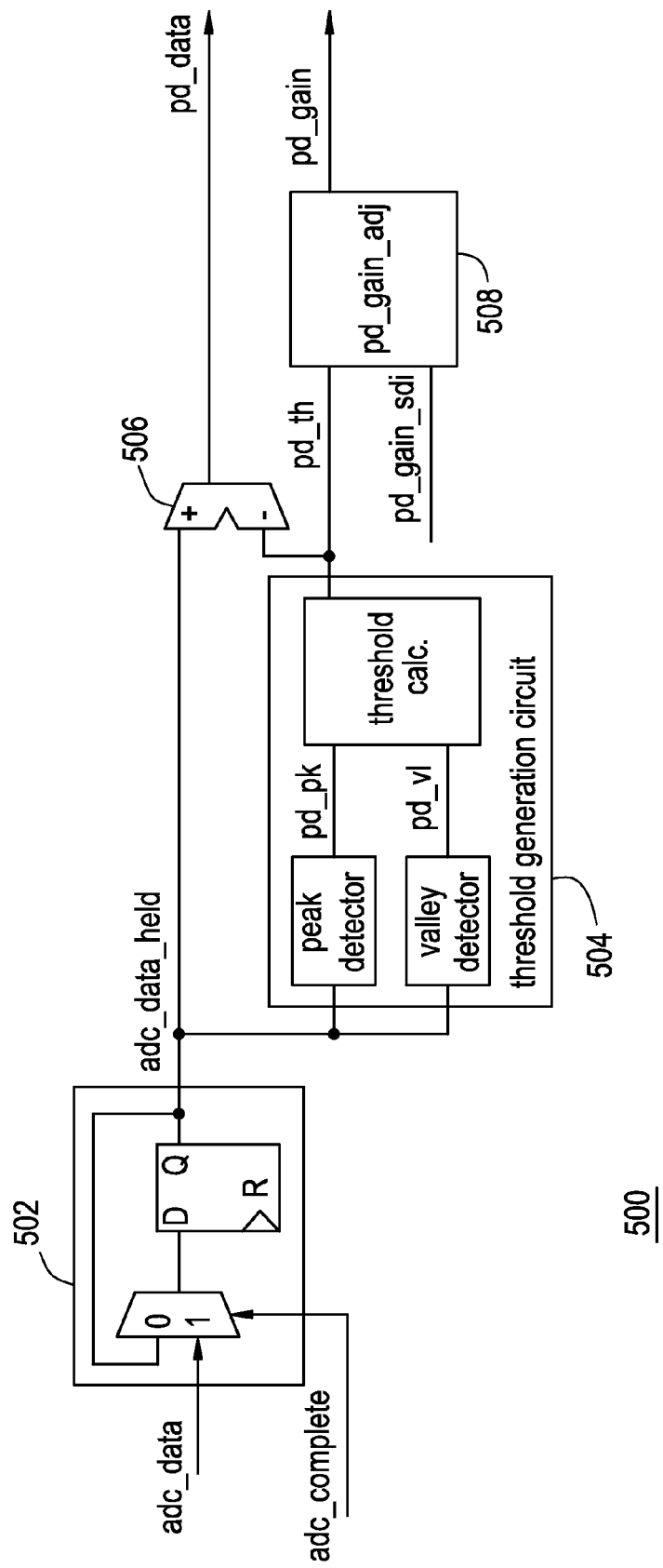
FIG. 5 is a block diagram of digital conditioning logic in accordance with the present invention.

FIG. 5 illustrates a block diagram of digital conditioning logic 500 that may be used to reduce the received ADC signal value, adc_data, to a single bit value pd_data. The digital conditioning logic 500 may comprise a digital register 502 to receive the data, adc_data, from the photodetection signal path pd_rx_top to provide a held value on the signal adc_data_held. The digital register 502 is configured to accept a new value on the adc_data signal when the adc_complete signal is asserted and to otherwise hold the last accepted value when the adc_complete signal is received. In this manner the system may disable the photodetection signal path once the data is latched to reduce system current consumption. The held data value may then be averaged, for example, by an integrate-and-dump average or other averaging methods implemented in digital logic, in the threshold generation circuit 504 to produce one or more thresholds on the signal pd_th. The held data value may then be compared, via comparator 506, to the one or more thresholds to produce a one-bit data value on the signal pd_data. It will be appreciated that the comparison operation may employ hysteresis or comparison to one or more thresholds to minimize noise on the output signal pd_data. The digital conditioning logic may further comprise a gain adjustment block pd_gain_adj 508 to set the gain of the automatic gain and low-pass filtering stage 406 in the photodetection signal path via the signal pd_gain, illustrated in FIG. 4, according to the calculated threshold values and/or according to the held data value. It is important to note that in this exemplary embodiment six bit words provide sufficient resolution over the dynamic range for blink detection while minimizing complexity.

In one exemplary embodiment, the threshold generation circuit 504 comprises a peak detector, a valley detector and a threshold calculation circuit. In this exemplary embodiment, the threshold and gain control values may be generated as follows. The peak detector and the valley detector are configured to receive the held value on signal adc_data_held. The peak detector is further configured to provide an output value, pd_pk, which quickly tracks increases in the adc_data_held value and slowly decays if the adc_data_held value decreases. The operation is analogous to that of a classic diode envelope detector, as is well-known in the electrical arts. The valley detector is further configured to provide an output value pd_vl which quickly tracks decreases in the adc_data_held value and slowly decays to a higher value if the adc_data_held value increases. The operation of the valley detector is also analogous to a diode envelope detector, with the discharge resistor tied to a positive power supply voltage. The threshold calculation circuit is configured to receive the pd_pl and pd_vl values and is further configured to calculate a mid-point threshold value pd_th_mid based on an average of the pd_pk and pd_vl values. The threshold generation circuit 504 provides the threshold value pd_th based on the mid-point threshold value pd_th_mid.

The threshold generation circuit 504 may be further adapted to update the values of the pd_pk and pd_vl levels in response to changes in the pd_gain value. If the pd_gain value increases by one step, then the pd_pk and pd_vl values are increased by a factor equal to the expected gain increase in the photodetection signal path. If the pd_gain value decreases by one step, then the pd_pk and pd_val values are decreased by a factor equal to the expected gain decrease in the photodetection signal path. In this manner the states of the peak detector and valley detectors, as held in the pd_pk and pd_vl values, respectively, and the threshold value pd_th as calculated from the pd_pk and pd_vl values are updated to match the changes in signal path gain, thereby avoiding discontinuities or other changes in state or value resulting only from the intentional change in the photodetection signal path gain.

In a further exemplary embodiment of the threshold generation circuit 504, the threshold calculation circuit may be further configured to calculate a threshold value pd_th_pk based on a proportion or percentage of the pd_pk value. In a preferred exemplary embodiment the pd_th_pk may be advantageously configured to be seven eighths of the pd_pk value, a calculation which may be implemented with a simple right shift by three bits and a subtraction as is well-known in the relevant art. The threshold calculation circuit may select the threshold value pd_th to be the lesser of pd_th_mid and pd_th_pk. In this manner, the pd_th value will never be equal to the pd_pk value, even after long periods of constant light incident on the photodiode which may result in the pd_pk and pd_vl values being equal. It will be appreciated that the pd_th_pk value ensures detection of a blink after long intervals. The behavior of the threshold generation circuit is further illustrated in FIG. 9, as discussed subsequently.

Figure 6:
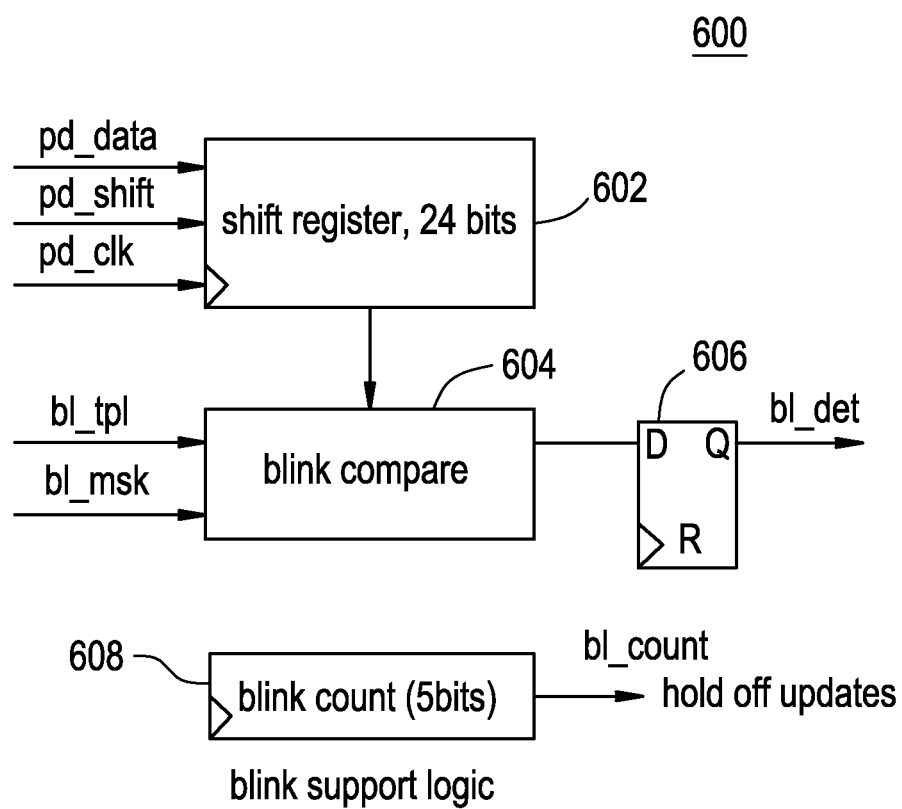
FIG. 6 is a block diagram of digital detection logic in accordance with the present invention.

FIG. 6 illustrates a block diagram of digital detection logic 600 that may be used to implement an exemplary digital blink detection algorithm in accordance with an embodiment of the present invention. The digital detection logic 600 may comprise a shift register 602 adapted to receive the data from the photodetection signal path pd_rx_top, FIG. 4, or from the digital conditioning logic, FIG. 5, as illustrated here on the signal pd_data, which has a one bit value. The shift register 602 holds a history of the received sample values, here in a 24-bit register. The digital detection logic 600 further comprises a comparison block 604, adapted to receive the sample history and one or more blink templates bl_tpl and blink masks bl_mask, and is configured to indicate a match to the one or more templates and masks on one or more output signals that may be held for later use. The output of the comparison block 604 is latched via a D flip-flop 606. The digital detection logic 600 may further comprise a counter 608 or other logic to suppress successive comparisons that may be on the same sample history set at small shifts due to the masking operations. In a preferred exemplary embodiment the sample history is cleared or reset after a positive match is found, thus requiring a full, new matching blink sequence to be sampled before being able to identify a subsequent match. The digital detection logic 600 may still further comprise a state machine or similar control circuitry to provide the control signals to the photodetection signal path and the ADC. In some exemplary embodiments the control signals may be generated by a control state machine that is separate from the digital detection logic 600. This control state machine may be part of the digital signal processing and system controller 410.

Figure 7:
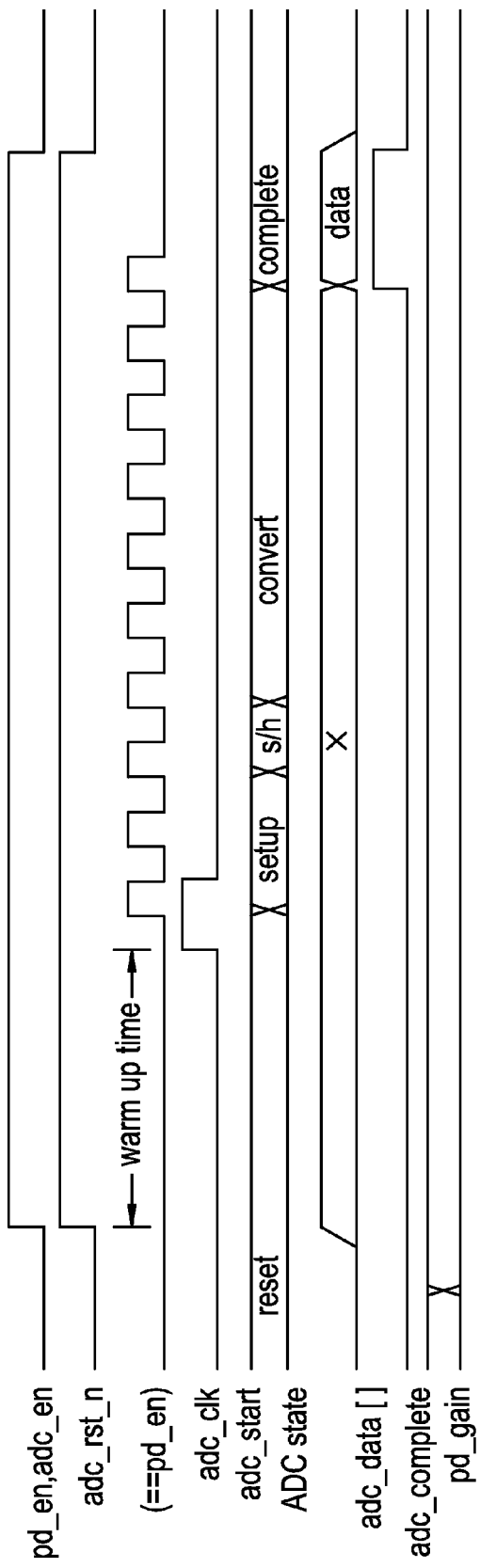
FIG. 7 is an exemplary timing diagram in accordance with the present invention.

FIG. 7 illustrates a timing diagram of the control signals provided from a blink detection subsystem to an ADC 408 (FIG. 4) used in a photodetection signal path. The enable and clock signals adc_en, adc_rst_n and adc_clk are activated at the start of a sample sequence and continue until the analog-to-digital conversion process is complete. In one exemplary embodiment the ADC conversion process is started when a pulse is provided on the adc_start signal. The ADC output value is held in an adc_data signal and completion of the process is indicated by the analog-to-digital converter logic on an adc_complete signal. Also illustrated in FIG. 7 is the pd_gain signal which is utilized to set the gain of the amplifiers before the ADC. This signal is shown as being set before the warm-up time to allow the analog circuit bias and signal levels to stabilize prior to conversion.

Figure 8:
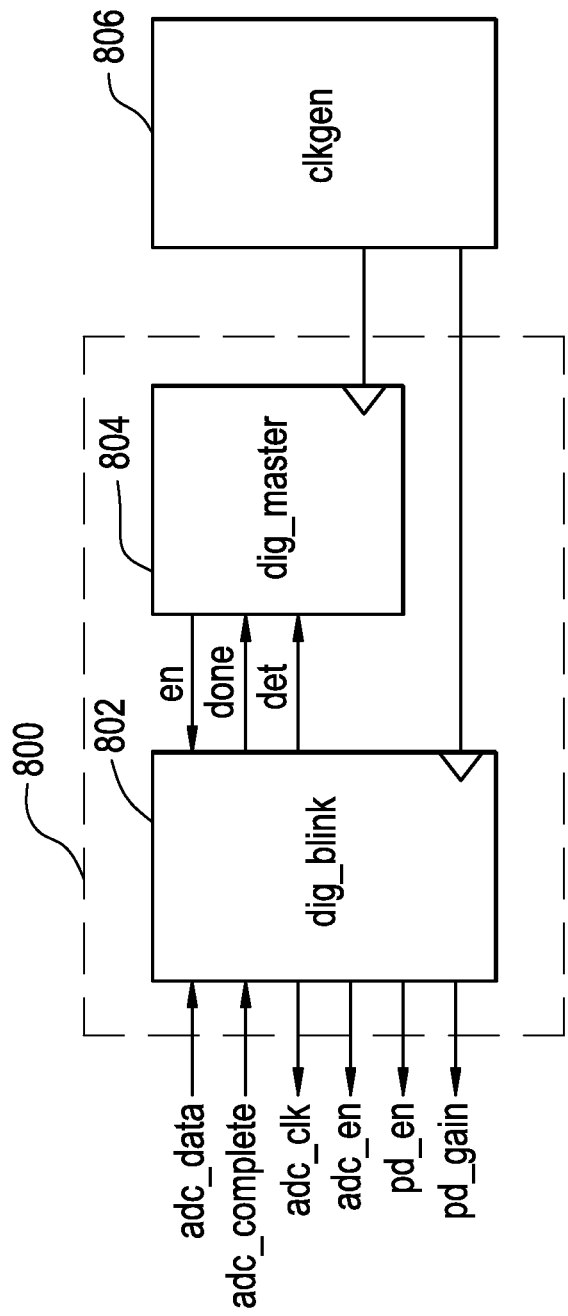
FIG. 8 is a diagrammatic representation of a digital system controller in accordance with the present invention.

FIG. 8 illustrates a digital system controller 800 comprising a digital blink detection subsystem dig_blink 802. The digital blink detection subsystem dig_blink 802 may be controlled by a master state machine dig_master 804 and may be adapted to receive clock signals from a clock generator clkgen 806 external to the digital system controller 800. The digital blink detection subsystem dig_blink 802 may be adapted to provide control signals to and receive signals from a photodetection subsystem as described above. The digital blink detection subsystem dig_blink 802 may comprise digital conditioning logic and digital detection logic as described above, in addition to a state machine to control the sequence of operations in a blink detection algorithm. The digital blink detection subsystem dig_blink 802 may be adapted to receive an enable signal from the master state machine 804 and to provide a completion or done indication and a blink detection indication back to the master state machine 804.

Figure 9A:
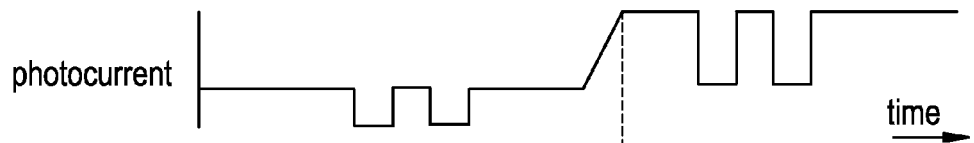
FIGS. 9A through 9G are exemplary timing diagrams for automatic gain control in accordance with the present invention.
Figure 9B:
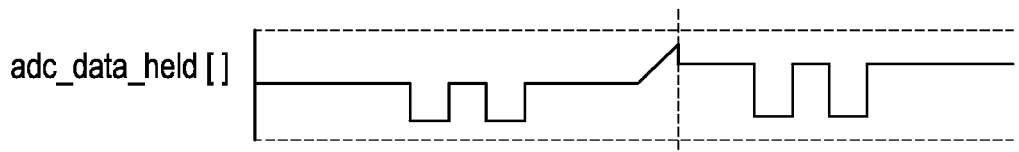
Figure 9C:
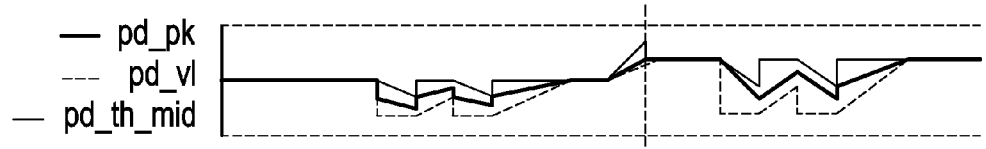
Figure 9D:
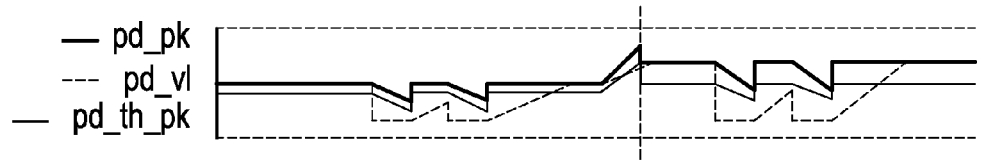
Figure 9E:
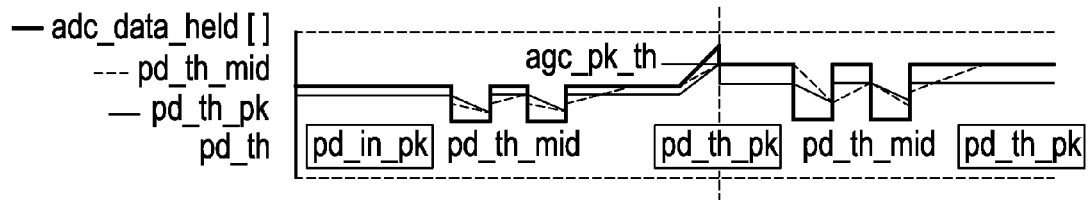
Figure 9F:
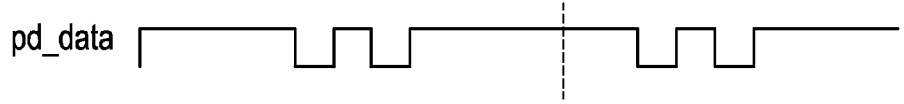
Figure 9G:
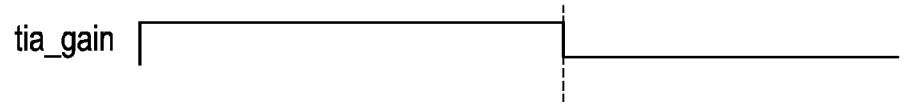

FIGS. 9A through 9G provide waveforms, to illustrate the operation of the threshold generation circuit and automatic gain control (FIG. 5). FIG. 9A illustrates an example of photocurrent versus time as might be provided by a photodiode in response to varying light levels. In the first portion of the plot, the light level and resulting photocurrent are relatively low compared to in the second portion of the plot. In both the first and second portions of the plot a double blink is seen to reduce the light and photocurrent. Note that the attenuation of light by the eyelid may not be one hundred (100) percent, but a lower value depending on the transmission properties of the eyelid for the wavelengths of light incident on the eye. FIG. 9B illustrates the adc_data_held value that is captured in response to the photocurrent waveform of FIG. 9A. For simplicity, the adc_data_held value is illustrated as a continuous analog signal rather than a series of discrete digital samples. It will be appreciated that the digital sample values will correspond to the level illustrated in FIG. 9B at the corresponding sample times. The dashed lines at the top and bottom of the plot indicate the maximum and minimum values of the adc_data and adc_data_held signals. The range of values between the minimum and maximum is also known as the dynamic range of the adc_data signal. As discussed below, the photodection signal path gain is different (lower) in the second portion of the plot. In general the adc_data_held value is directly proportional to the photocurrent, and the gain changes only affect the ration or the constant of proportionality. FIG. 9C illustrates the pd_pk, pd_vl and pd_th_mid values calculated in response to the adc_data_held value by the threshold generation circuit. FIG. 9D illustrates the pd_pk, pd_vl and pd_th_pk values calculated in response to the adc_data_held value in some exemplary embodiments of the threshold generation circuit. Note that the pd_th_pk value is always some proportion of the pd_pk value. FIG. 9E illustrates the adc_data_held value with the pd_th_mid and pd_th_pk values. Note that during long periods of time where the adc_data_held value is relatively constant the pd_th_mid value becomes equal to the adc_data_held value as the pd_vl value decays to the same level. The pd_th_pk value always remains some amount below the adc_data_held value. Also illustrated in FIG. 9E is the selection of pd_th where the pd_th value is selected to be the lower of pd_th_pk and pd_th_mid. In this way the threshold is always set some distance away from the pd_pk value, avoiding false transitions on pd_data due to noise on the photocurrent and adc_data held signals. FIG. 9F illustrates the pd_data value generated by comparison of the adc_data_held value to the pd_th value. Note that the pd_data signal is a two-valued signal which is low when a blink is occurring. FIG. 9G illustrates a value of tia_gain versus time for these example waveforms. The value of tia_gain is set lower when the pd_th starts to exceed a high threshold shown as agc_pk_th in FIG. 9E. It will be appreciated that similar behavior occurs for raising tia_gain when pd_th starts to fall below a low threshold. Looking again at the second portion of each of the FIGS. 9A through 9E the effect of the lower tia_gain is clear. In particular note that the adc_data_held value is maintained near the middle of the dynamic range of the adc_data and adc_data_held signals. Further, it is important to note that the pd_pk and pd_vl values are updated in accordance with the gain change as described above such that discontinuities are avoided in the peak and valley detector states and values due solely to changes in the photodetection signal path gain.

Figure 10:
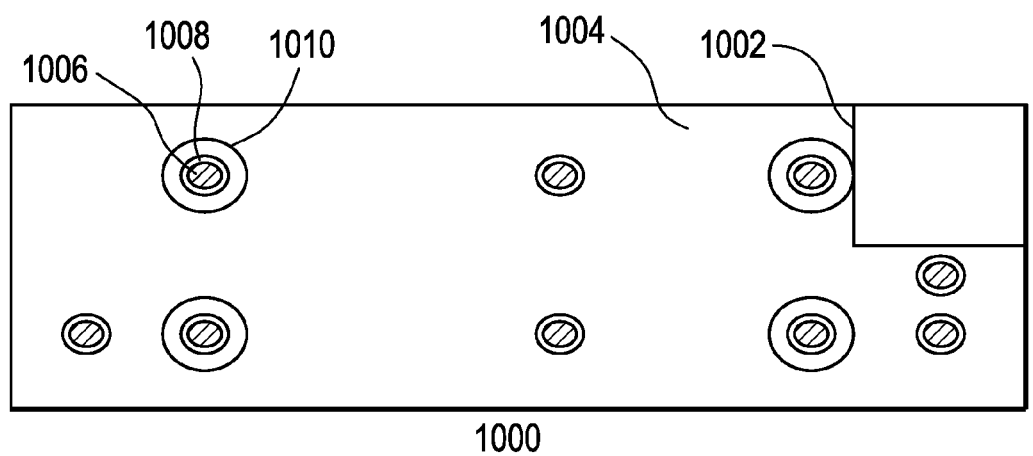
FIG. 10 is a diagrammatic representation of light-blocking and light-passing regions on an exemplary integrated circuit die in accordance with the present invention.

FIG. 10 illustrates exemplary light-blocking and light-passing features on an integrated circuit die 1000. The integrated circuit die 1000 comprises a light passing region 1002, a light blocking region 1004, bond pads 1006, passivation openings 1008, and light blocking layer openings 1010. The light-passing region 1002 is located above the photosensors (not illustrated), for example an array of photodiodes implemented in the semiconductor process. In a preferred exemplary embodiment, the light-passing region 1002 permits as much light as possible to reach the photosensors thereby maximizing sensitivity. This may be done through removing polysilicon, metal, oxide, nitride, polyimide, and other layers above the photoreceptors, as permitted in the semiconductor process utilized for fabrication or in post processing. The light-passing area 1002 may also receive other special processing to optimize light detection, for example an anti-reflective coating, filter, and/or diffuser.

The light-blocking region 1004 may cover other circuitry on the die which does not require light exposure. The performance of the other circuitry may be degraded by photocurrents, for example shifting bias voltages and oscillator frequencies in the ultra-low current circuits required for incorporation into contact lenses, as mentioned previously. The light-blocking region 1004 is preferentially formed with a thin, opaque, reflective material, for example aluminum or copper already use in semiconductor wafer processing and post-processing. If implemented with metal, the material forming the light-blocking region 1004 must be insulated from the circuits underneath and the bond pads 1006 to prevent short-circuit conditions. Such insulation may be provided by the passivation already present on the die as part of normal wafer passivation, e.g. oxide, nitride, and/or polyimide, or with other dielectric added during post-processing. Masking permits light blocking layer openings 1010 so that conductive light-blocking metal does not overlap bond pads on the die. The light-blocking region 1004 is covered with additional dielectric or passivation to protect the die and avoid short-circuits during die attachment. This final passivation has passivation openings 1008 to permit connection to the bond pads 1006.

Figure 11:
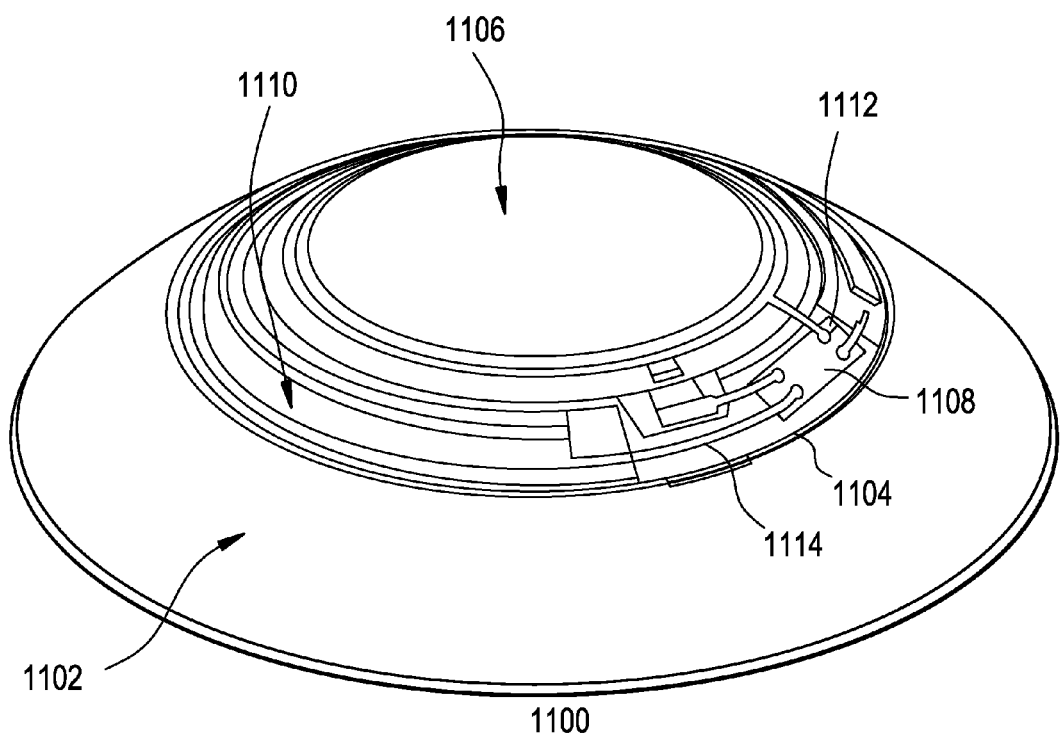
FIG. 11 is a diagrammatic representation of an exemplary electronic insert, including a blink detector, for a powered contact lens in accordance with the present invention.

FIG. 11 illustrates an exemplary contact lens with an electronic insert comprising a blink detection system in accordance with the present embodiments (invention). The contact lens 1100 comprises a soft plastic portion 1102 which comprises an electronic insert 1104. This insert 1104 includes a lens 1106 which is activated by the electronics, for example focusing near or far depending on activation. Integrated circuit 1108 mounts onto the insert 1104 and connects to batteries 1110, lens 1106, and other components as necessary for the system. The integrated circuit 1108 includes a photosensor 1112 and associated photodetector signal path circuits. The photosensor 1112 faces outward through the lens insert and away from the eye, and is thus able to receive ambient light. The photosensor 1112 may be implemented on the integrated circuit 1108 (as shown) for example as a single photodiode or array of photodiodes. The photosensor 1112 may also be implemented as a separate device mounted on the insert 1104 and connected with wiring traces 1114. When the eyelid closes, the lens insert 1104 including photodetector 1112 is covered, thereby reducing the light level incident on the photodetector 1112. The photodetector 1112 is able to measure the ambient light to determine if the user is blinking or not.

Additional embodiments of the blink detection algorithm may allow for more variation in the duration and spacing of the blink sequence, for example by timing the start of a second blink based on the measured ending time of a first blink rather than by using a fixed template or by widening the mask "don't care" intervals (0 values).

It will be appreciated that the blink detection algorithm may be implemented in digital logic or in software running on a microcontroller. The algorithm logic or microcontroller may be implemented in a single application-specific integrated circuit, ASIC, with photodetection signal path circuitry and a system controller, or it may be partitioned across more than one integrated circuit.

It is important to note that the blink detection system of the present invention has broader uses than for vision diagnostics, vision correction and vision enhancement. These broader uses include utilizing blink detection to control a wide variety of functionality for individuals with physical disabilities. The blink detection may be set up on-eye or off-eye.

In accordance with another exemplary embodiment, a powered or electronic ophthalmic lens may incorporate a pupil position and convergence detection system. In the process of accommodation, the crystalline lens geometry is changed via action of the ciliary muscle to increase its add power as the individual attempts to focus on a near distance object. At the same time as the crystalline lens accommodates, two other actions occur; namely, each eye (pupil) moves slightly inward towards the nose, convergence, and the pupils get a bit smaller (miosis). The changes in the crystalline lens, convergence and miosis are generally referred to as the accommodative reflex. In other words, when an individual focuses on a near object, for example when reading, his or her pupils converge to fix the gaze of both eyes on the same location. This phenomenon is based on the geometry of the system which is a triangle formed from the distance between the two eyes and the distance from each eye to the object. A more detailed description is given subsequently. Because of the correlation between pupil convergence and focusing on near objects, pupil convergence may be utilized to trigger actions in an electronic ophthalmic lens, for example, changing the power of a variable power optic to allow an individual with presbyopia to focus on near distance objects. It is also important to note that the sensed data, in addition to or in alternate use may simply be utilized as part of a collection process rather than as a triggering event. For example, the sensed data may be collected, logged and utilized in treating medical conditions. In other words, it should also be appreciated that a device utilizing such a sensor may not change state in a manner visible to the user; rather the device may simply log data. For example, such a sensor could be used to determine if a user has the proper iris response throughout a day or if a problematic medical condition exists.

Figure 12A:
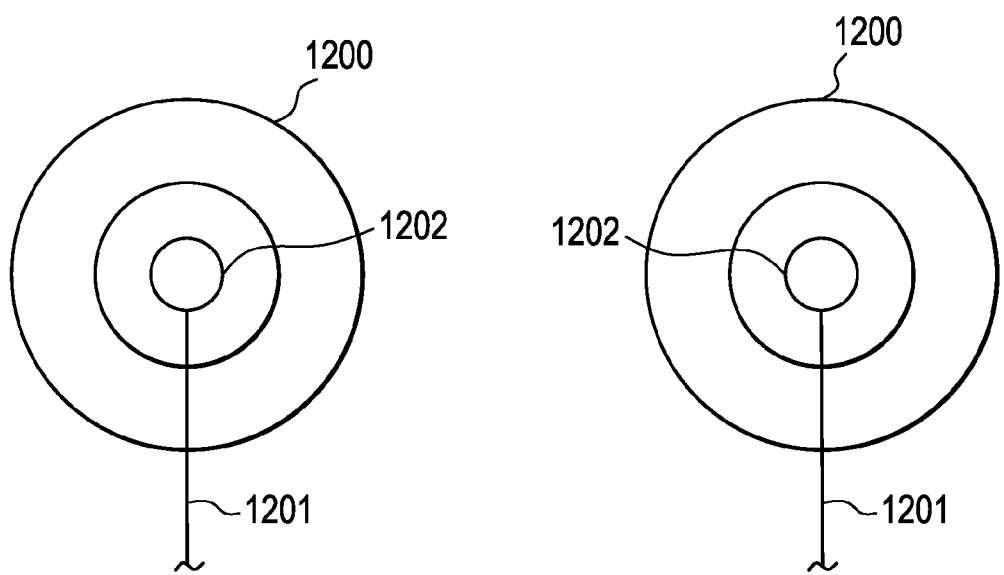
FIG. 12A is a diagrammatic, front perspective representation of the eyes of an individual gazing at a distant object.
Figure 12B:
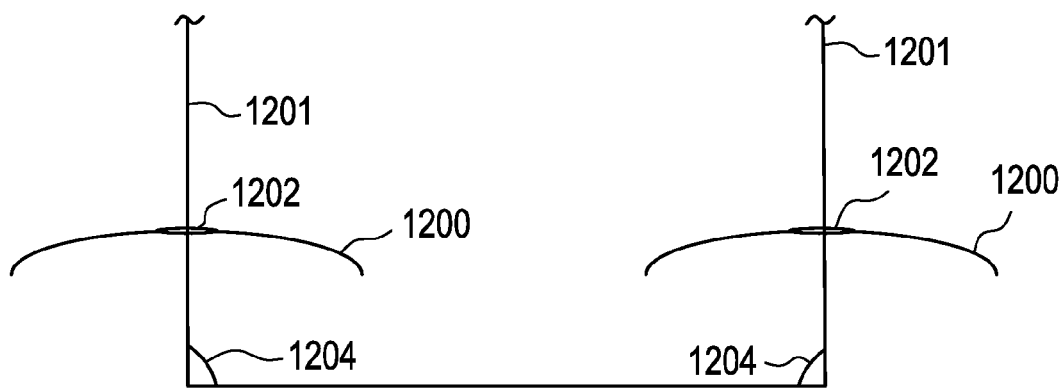
FIG. 12B is a diagrammatic, top perspective representation of the eyes of FIG. 12A.

FIGS. 12A and 12B illustrate different views of the two eyes 1200 of an individual who is gazing at a distant object which requires far focus, for example, driving a car, instead of near focus, for example, reading a book. FIG. 12A illustrates a front perspective of the eyes 1200, whereas FIG. 12B illustrates a top perspective of the eyes 1200. While gazing at a distant object, not illustrated, the pupils 1202 are centered and track together. Lines 1201 between the pupils 1202 and the object under observation are parallel as is shown by angles 1204 both being ninety (90) degrees. This is because the distance between the two eyes 1200 on any individual is much less than the distance from the eyes 1200 to the object under observation. As an individual tracks the movement of a distant object, although the eyes 1200 move, the angles 1204 remain very close to ninety (90) degrees, again because the distance between the two eyes 1200 is much less than the distance from the eyes 1200 to the object under observation.

Figure 13A:
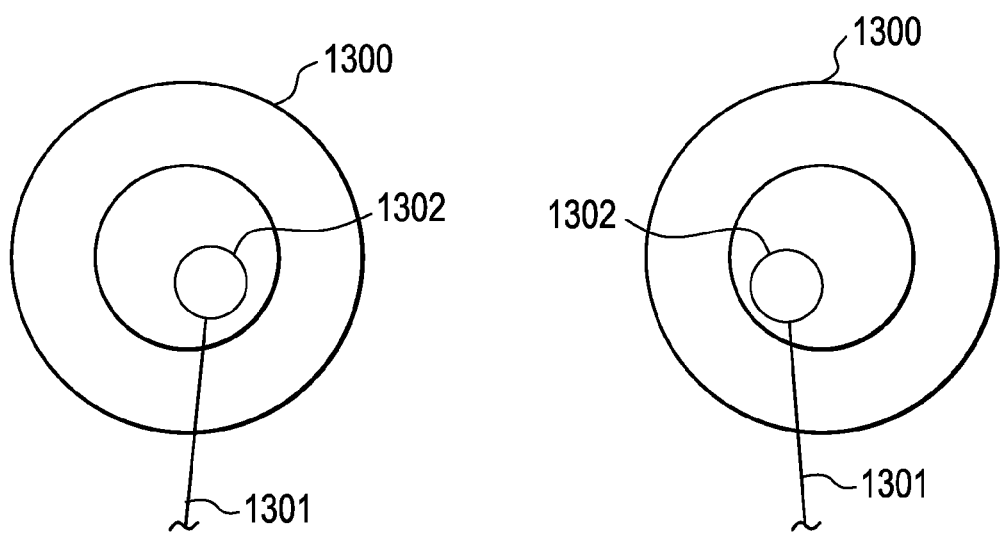
FIG. 13A is a diagrammatic, front perspective representation of the eyes of an individual gazing at a near object.
Figure 13B:
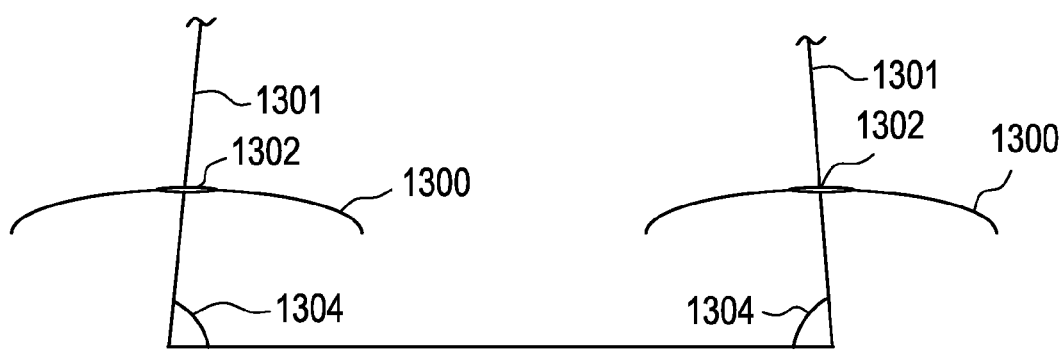
FIG. 13B is a diagrammatic, top perspective representation of the eyes of FIG. 13A.

FIGS. 13A and 13B illustrate a pair of eyes 1300 substantially similar to those illustrated in FIGS. 12A and 12B, with the exception that in this example the object under observation, not illustrated, is close or near rather than distant. Since the distance between the eyes 1300 is now appreciable relative to the distance from the eyes 1300 to the object under observation, the eyes 1300 converge to keep the object under observation within the field of view. As illustrated, via exaggeration, pupils 1302 converge and move closer together. Lines 1301 drawn between the pupils and the object under observation are no longer parallel, and the angles 1304 are less than ninety (90) degrees. This phenomena may be easily observed by having a subject first focus on his or her finger at an approximate distance of two (2) feet with his or her arm fully extended. As the subject brings his or her finger closer, his or her eyes will converge towards his or her nose becoming "cross-eyed."

Figure 14:
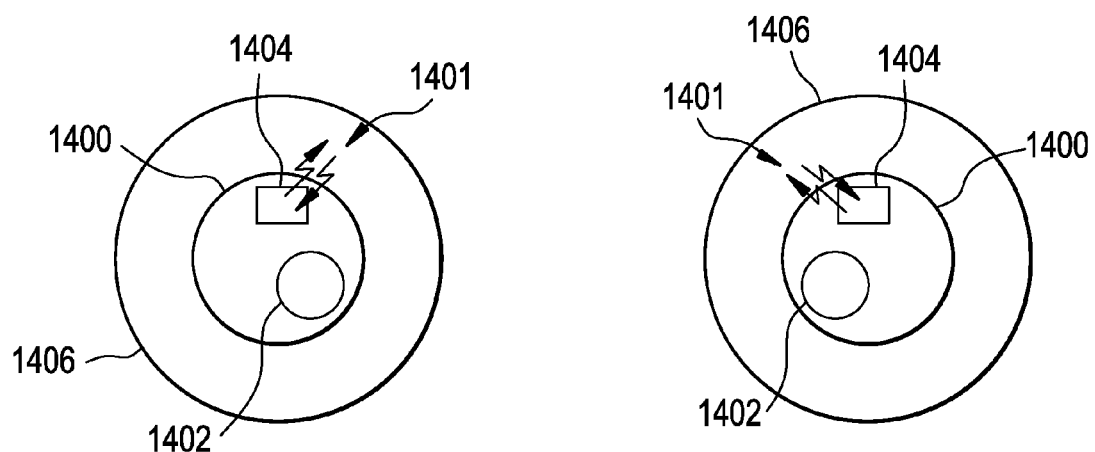
FIG. 14 is a diagrammatic representation of two exemplary pupil position and convergence sensors having a communication channel for synchronizing operation between two eyes in accordance with the present invention.

FIG. 14 illustrates a system by which the convergence described with respect to FIGS. 12A, 12B, 13A and 13B may be sensed and communicated between a pair of contact lenses 1400. Pupils 1402 are illustrated converged for near object viewing. Pupil position and convergence detection systems 1404 incorporated within contact lenses 1400 that are positioned on eyes 1406 track the position of the pupils 1402 and/or the contact lenses 1400, for example, with reverse-facing photodetectors to observe the pupils 1402 or with accelerometers to track movement of the eyes 1406 and hence the pupils 1402. The pupil position and convergence detector systems 1404 may comprise several components forming a more complex system, for example a 3-axis accelerometer, signal conditioning circuitry, a controller, memory, power supply, and a transceiver as is described in detail subsequently. Communication channel 1401 between the two contact lenses 1400 allows the pupil position and convergence detection systems 1404 to synchronize on pupil position. Communication may also take place with an external device, for example, spectacle glasses or a smartphone. Communication between the contact lenses 1400 is important to detect convergence. For example, without knowing the position of both pupils 1402, simply gazing down to the left may be detected as convergence by the right eye since the pupil 1402 has similar movement for both actions. However, if the right pupil is detected moving down to the left while the pupil of the left eye is detected moving down to the right, convergence may be construed. Communication between the two contact lenses 1400 may take the form of absolute or relative position, or may simply be a "convergence suspected" signal if the eye moves in the expected direction of convergence. In this case, if a given contact lens detects convergence itself and receives a convergence indication from the adjacent contact lens, it may activate a change in stage, for example, switching a variable-focus or variable power optic equipped contact lens to the near distance state to support reading. Other information useful for determining the desire to accommodate (focus near), for example, lid position and ciliary muscle activity, may also be transmitted over the communication channel 1401 if the contact lenses are so equipped. It should also be appreciated that communication over the channel 1401 could comprise other signals sensed, detected, or determined by each lens 1406 and used for a variety of purposes, including vision correction, vision enhancement, entertainment, and novelty.

In accordance with one exemplary embodiment, a digital communication system comprises a number of elements which when implemented, may take on any number of forms. The digital communication system generally comprises an information source, a source encoder, a channel encoder, a digital modulator, a channel, a digital demodulator, a channel decoder and a source decoder.

The information source may comprise any device that generates information and/or data that is required by another device or system. The source may be analog or digital. If the source is analog, its output is converted into a digital signal comprising a binary string. The source encoder implements a process of efficiently converting the signal from the source into a sequence of binary digits. The information from the source encoder is then passed into a channel encoder where redundancy is introduced into the binary information sequence. This redundancy may be utilized at the receiver to overcome the effects of noise, interference and the like encountered on the channel. The binary sequence is then passed to a digital modulator which in turn converts the sequence into analog electrical signals for transmission over the channel. Essentially, the digital modulator maps the binary sequences into signal waveforms or symbols. Each symbol may represent the value of one or more bits. The digital modulator may modulate a phase, frequency or amplitude of a high frequency carrier signal appropriate for transmission over or through the channel. The channel is the medium through which the waveforms travel, and the channel may introduce interference or other corruption of the waveforms. In the case of the wireless communication system, the channel is the atmosphere. The digital demodulator receives the channel-corrupted waveform, processes it and reduces the waveform to a sequence of numbers that represent, as nearly as possible, the transmitted data symbols. The channel decoder reconstructs the original information sequence from knowledge of the code utilized by the channel encoder and the redundancy in the received data. The source decoder decodes the sequence from knowledge of the encoding algorithm, wherein the output thereof is representative of the source information signal.

It is important to note that the above described elements may be realized in hardware, in software or in a combination of hardware and software. In addition, the communication channel may comprise any type of channel, including wired and wireless. In wireless, the channel may be configured for high frequency electromagnetic signals, low frequency electromagnetic signals, visible light signals and infrared light signals.

FIGS. 15 A and B are diagrammatic representations of an exemplary pupil position and convergence detection system 1500 for control of one or more aspects of a powered ophthalmic lens. Sensor 1502 detects the movement and/or position of the pupil or, more generally, the eye. The sensor 1502 may be implemented as a multi-axis accelerometer on a contact lens 1501. With the contact lens 1501 being affixed to the eye and generally moving with the eye, an accelerometer on the contact lens 1501 may track eye movement. The sensor 1502 may also be implemented as a rear-facing camera or sensor which detects changes in images, patterns, or contrast to track eye movement. Alternately, the sensor 1502 may comprise neuromuscular sensors to detect nerve and/or muscle activity which moves the eye in the socket. There are six muscles attached to each eye globe which provide each eye with a full range of movement and each muscle has its own unique action or actions. These six muscles are innervated by one of the three cranial nerves. It is important to note that any suitable device may be utilized as the sensor 1502, and more than a single sensor 1502 may be utilized. The output of the sensor 1502 is acquired, sampled, and conditioned by signal processor 1504. The signal processor 1504 may include any number of devices including an amplifier, a transimpedance amplifier, an analog-to-digital converter, a filter, a digital signal processor, and related circuitry to receive data from the sensor 1502 and generate output in a suitable format for the remainder of the components of the system 1500. The signal processor 1504 may be implemented utilizing analog circuitry, digital circuitry, software, and/or preferably a combination thereof. It should be appreciated that the signal processor 1504 is co-designed with the sensor 1502 utilizing methods that are known in the relevant art, for example, circuitry for acquisition and conditioning of an accelerometer are different than the circuitry for a muscle activity sensor or optical pupil tracker. The output of the signal processor 1504 is preferentially a sampled digital stream and may include absolute or relative position, movement, detected gaze in agreement with convergence, or other data. System controller 1506 receives input from the signal processor 1504 and uses this information, in conjunction with other inputs, to control the electronic contact lens 1501. For example, the system controller 1506 may output a signal to an actuator 1508 that controls a variable power optic in the contact lens 1501. If, for example, the contact lens 1501 is currently in a far focus state and the sensor 1502 detects convergence, the system controller 1506 may command the actuator 1508 to change to a near focus state. System controller 1506 may both trigger the activity of sensor 1502 and the signal processor 1504 while receiving output from them. A transceiver 1510 receives and/or transmits communication through antenna 1502. This communication may come from an adjacent contact lens, spectacle lenses, or other devices. The transceiver 1510 may be configured for two way communication with the system controller 1506. Transceiver 1510 may contain filtering, amplification, detection, and processing circuitry as is common in transceivers. The specific details of the transceiver 1510 are tailored for an electronic or powered contact lens, for example the communication may be at the appropriate frequency, amplitude, and format for reliable communication between eyes, low power consumption, and to meet regulatory requirements. Transceiver 1510 and antenna 1512 may work in the radio frequency (RF) bands, for example 2.4 GHz, or may use light for communication. Information received from transceiver 1510 is input to the system controller 1506, for example, information from an adjacent lens which indicates convergence or divergence. System controller 1506 uses input data from the signal processor 1504 and/or transceiver 1510 to decide if a change in system state is required. The system controller 1506 may also transmit data to the transceiver 1510, which then transmits data over the communication link via antenna 1512. The system controller 1506 may be implemented as a state machine, on a field-programmable gate array, in a microcontroller, or in any other suitable device. Power for the system 1500 and components described herein is supplied by a power source 1514, which may include a battery, energy harvester, or similar device as is known to one of ordinary skill in the art. The power source 1514 may also be utilized to supply power to other devices on the contact lens 1501.

The exemplary pupil position and convergence detection system 1500 of the present invention is incorporated and/or otherwise encapsulated and insulated from the saline contact lens 1501 environment.

Figure 15A:
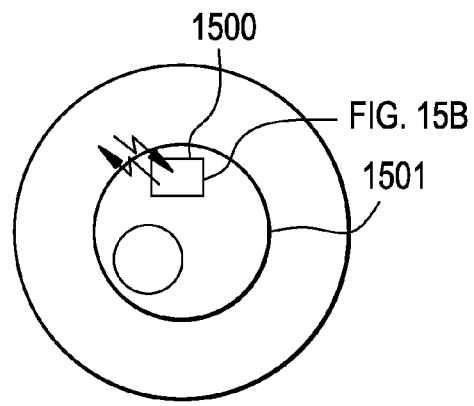
FIG. 15A is a diagrammatic representation of an exemplary pupil position and convergence detection system incorporated into a contact lens in accordance with the present invention.
Figure 15B:
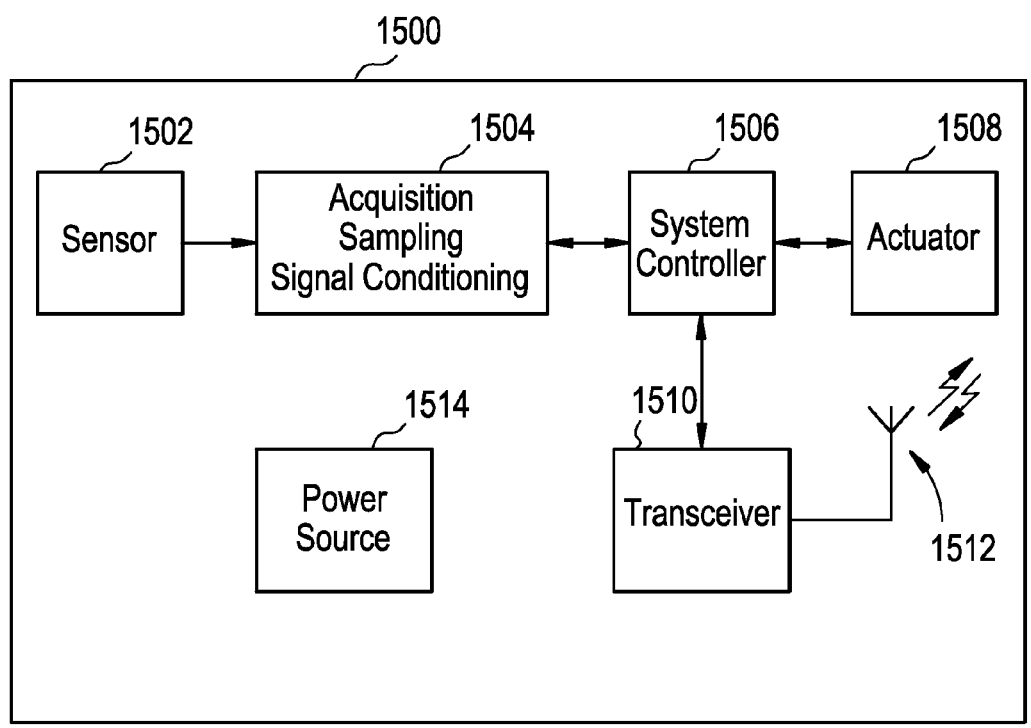
FIG. 15B is an enlarged view of the exemplary pupil position and convergence detection system of FIG. 15A.
Figure 16:
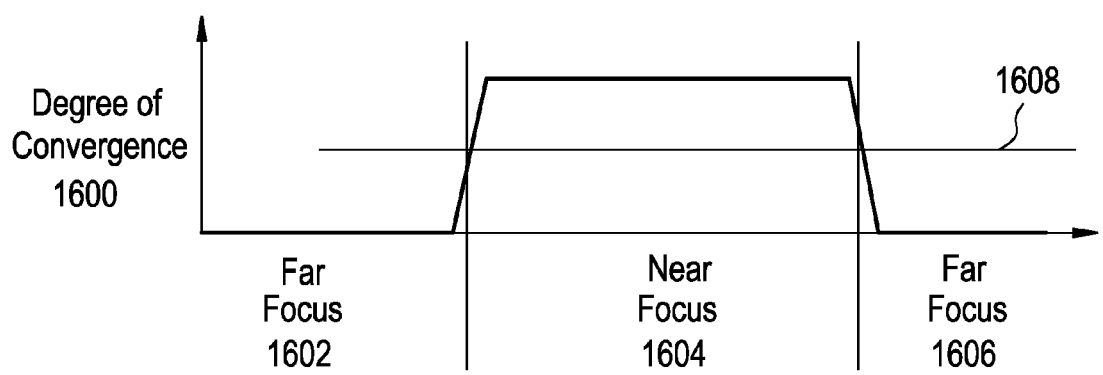
FIG. 16 is a diagrammatic representation of an exemplary plot of the correlation between pupil convergence and focal distance.

FIG. 16 illustrates an exemplary, simplified correlation between convergence 1600 and focal length states 1602, 1604, and 1606 as is commonly documented in the ophthalmic literature. When in the far focus state 1602 and 1606, as described with respect to FIGS. 12A and 12B, the degree of convergence is low. When in the near focus state 1604, as described with respect to FIGS. 13A and 13B, the degree of convergence is high. A threshold 1608 may be set in the system controller (element 1506 of FIG. 15) to change the state of the electronic ophthalmic lens, for example, focusing a variable optic with add power when the threshold is passed going positive then focusing the variable optic with no add power when the threshold is passed going negative.

Eye tracking is the process of determining either or both where an individual is looking, point of gaze, or the motion of an eye relative to the head. An individual's gaze direction is determined by the orientation of the head and the orientation of the eyes. More specifically, the orientation of an individual's head determines the overall direction of the gaze while the orientation of the individual's eyes determines the exact gaze direction which in turn is limited by the orientation of the head. Information of where an individual is gazing provides the ability to determine the individual's focus of attention and this information may be utilized in any number of disciplines or application, including cognitive science, psychology, human-computer interaction, marketing research and medical research. For example, eye gaze direction may be utilized as a direct input into a controller or computer to control another action. In other words, simple eye movements may be utilized to control the actions of other devices, including highly complex functions. Simple eye movements may be utilized in a manner similar to "swipes" which have become common in touch-screen and smartphone applications, for example, swiping to unlock a device, change applications, change pages, zoom in or out and the like. Eye gaze tracking systems are presently utilized to restore communication and functionality to those who are paralyzed, for example, using eye movements to operate computers. Eye tracking or gaze tracking may also be utilized in any number of commercial applications, for example, what individuals are paying attention to when they are watching television, browsing websites and the like. The data collected from this tracking may be statistically analyzed to provide evidence of specific visual patterns. Accordingly, information garnered from detecting eye or pupil movement may be utilized in a wide range applications. Once again, it is also important to note that the sensed data, in addition to or in alternate use may simply be utilized as part of a collection process rather than as a triggering event. For example, the sensed data may be collected, logged and utilized in treating medical conditions. In other words, it should also be appreciated that a device utilizing such a sensor may not change state in a manner visible to the user; rather the device may simply log data. For example, such a sensor could be used to determine if a user has the proper iris response throughout a day or if a problematic medical condition exists.

It is important to note, that eye tracking in accordance with the present invention may be set up for gross or fine tracking monitoring.

There are a number of currently available devices for tracking eye movement, including video-based eye trackers, search coils and arrangements for generating electrooculograms. Search coils or inductive sensors are devices which measure the variations of the surrounding magnetic fields. Essentially, a number of coils may be imbedded into a contact lens type device and the polarity and amplitude of the current generated in the coils varies with the direction and angular displacement of the eye. An electrooculogram is generated by a device for the detection of eye movement and eye position based on the difference in electrical potential between electrodes placed on either side of the eye. All of these devices are not suitable for use with a wearable, comfortable electronic ophthalmic lens or powered contact lens. Therefore, in accordance with another exemplary embodiment, the present invention is directed to a powered contact lens comprising a gaze sensor incorporated directly into the contact lens.

Figure 17A:
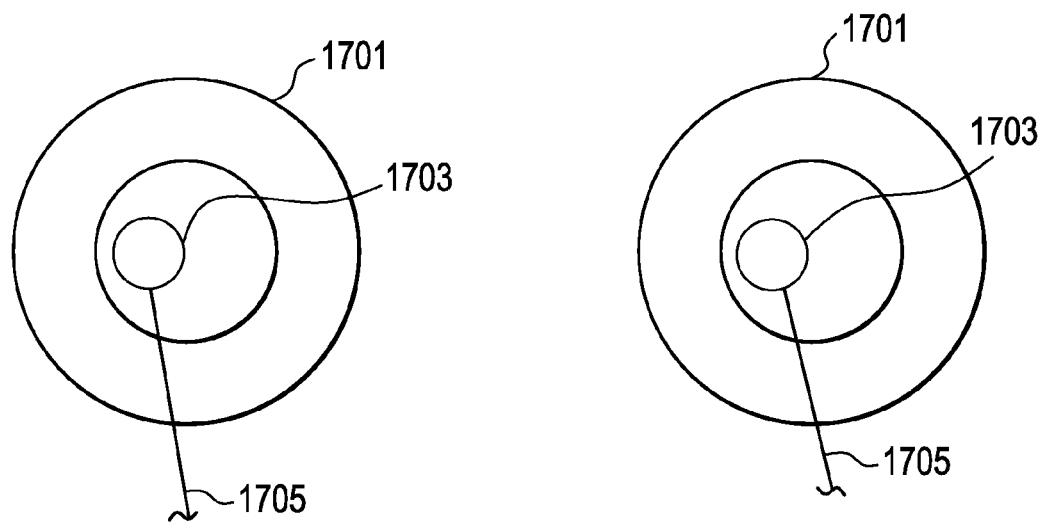
FIG. 17A is a diagrammatic, front perspective representation of the eyes of an individual gazing to the right.
Figure 17B:
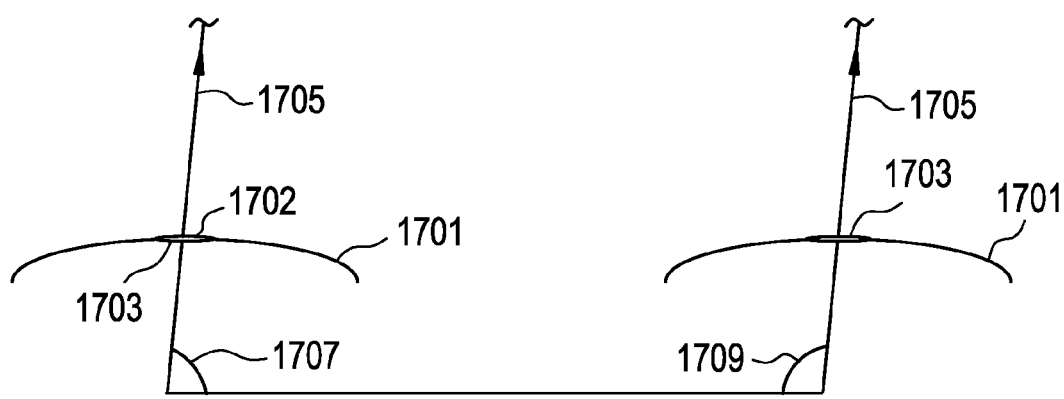
FIG. 17B is a diagrammatic, top perspective representation of the eyes of FIG. 17A.

FIGS. 17A and 17B illustrate a pair of eyes 1701 substantially similar to those illustrated in FIGS. 12A and 12B, with the exception that in this example the object under observation, not illustrated, is to the right of the user. FIG. 17A illustrates a front perspective of the eyes 1701, whereas FIG. 17B illustrates a top perspective of the eyes 1701. The position to the right is used for illustrative purposes, but it should be appreciated that the object under observation could be at any visible point in three-dimension space with the corresponding changes in eye gaze. As illustrated, via exaggeration, pupils 1703 both face toward the right. Lines 1705 drawn between the pupils 1703 and the object under observation are almost parallel since the object is illustrated to be much farther from the eyes 1701 than the distance between the eyes 1701. Angle 1707 is less than ninety (90) degrees whereas angle 1709 is greater than ninety (90) degrees. These angles are in contrast to previous figures where the angles were either both ninety (90) degrees, when gazing straight ahead at a distant object, or both less than ninety degrees, when gazing straight ahead at a nearby object. As is illustrated in two dimensions, the angle may be used to determine gaze position or, more generally, samples of eye movement may be utilized to determine absolute and relative position and movement of eye gaze.

Figure 18:
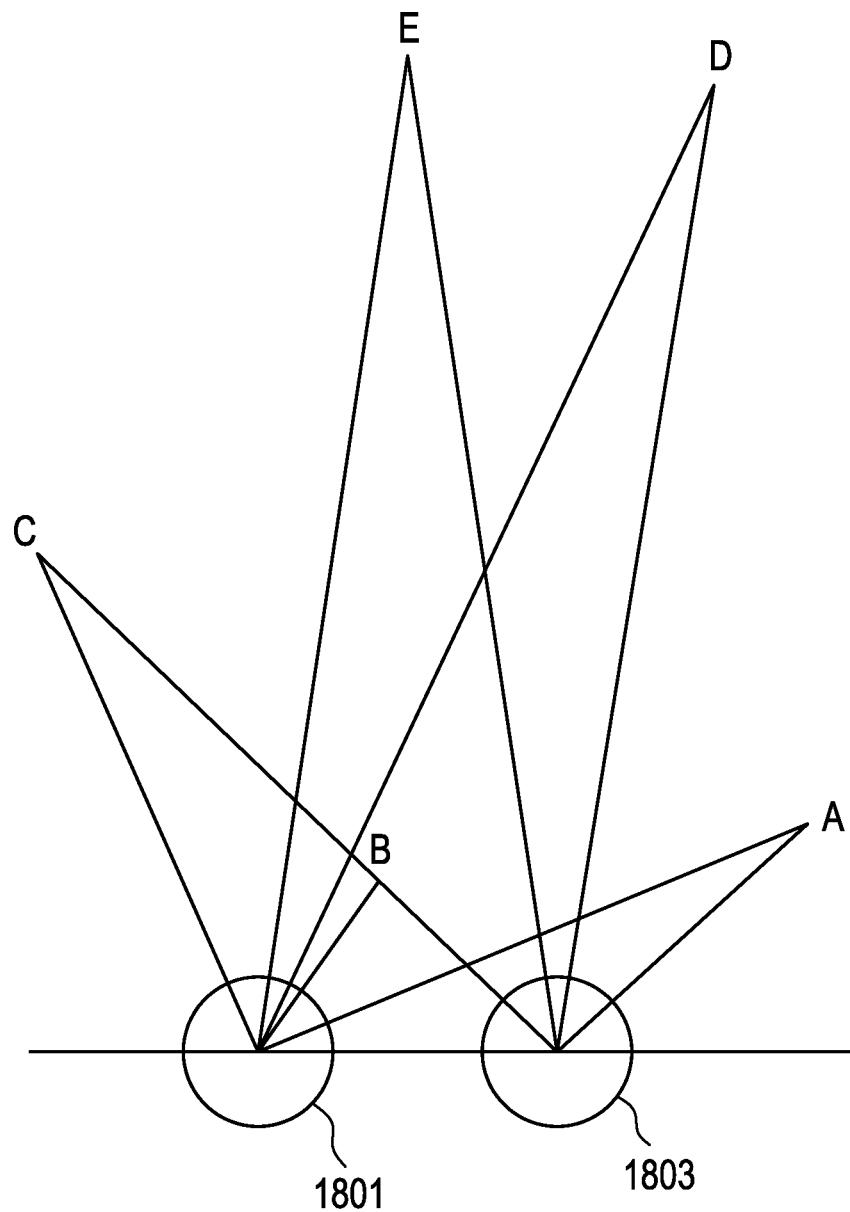
FIG. 18 is a diagrammatic representation of the geometry associated with various gaze directions in two dimensions in accordance with the present invention.

FIG. 18 illustrates the geometric systems associated with various gaze directions. FIG. 18 is a top view. Eyes 1801 and 1803 are shown gazing upon various targets labeled A, B, C, D, and E. A line connects each eye 1801 and 1803 to each target. A triangle is formed by each of the two lines connecting the eyes 1801 and 1803 with a given target in addition to a line connecting both eyes 1801 and 1803. As may be seen in the illustration, the angles between the direction of gaze in each eye 1801 and 1803 and the line between the two eyes 1801 and 1803 varies for each target. These angles may be measured by the sensor system, determined from indirect sensor measurements, or may only be shown for illustrative purposes. Although shown in two-dimensional space for simplicity of illustration, it should be apparent that gaze occurs in three-dimensional space with the corresponding addition of an additional axis. Targets A and B are shown relatively near to the eyes 1801 and 1803, for example, to be read with near-focus accommodation. Target A is to the right of both eyes 1801 and 1803, hence both eyes 1801 and 1803 are pointing right. Measuring the angle formed anti-clockwise between the horizontal axis, illustrated collinear with the line connecting the two eyes 1801 and 1803, and direction of gaze, both angles are acute for target A. Now referring to target B the eyes 1801 and 1803 are converged on a target in front of and between both eyes 1801 and 1803. Hence the angle, previously defined as anti-clockwise from the horizontal axis and the direction of gaze, is obtuse for the right eye 1803 and acute for the left eye 1801. A suitable sensor system will differentiate the positional difference between targets A and B with suitable accuracy for the application of concern. Target C is shown at intermediate distance for the special case of the right eye 1803 having the same direction of gaze and angle as target B. The gaze direction varies between targets B and C allowing a gaze direction determination system using inputs from both eyes 1801 and 1803 to determine the direction of gaze. Further, a case could be illustrated where another target F lies above target B in three-dimensional space. In such an example, projected into the two-dimensional illustration shown in FIG. 18, the angles from the horizontal axis would be identical to those illustrated for target B. However, the angles normal to the page extending in three-dimensional space would not be equal between the targets. Finally, targets D and E are shown as distant objects. These examples illustrate that as the object under gaze is farther away, the angular difference at the eyes 1801 and 1803 between distant points becomes smaller. A suitable system for detecting gaze direction would have sufficient accuracy to differentiate between small, distant objects.

The direction of gaze may be determined by any number of suitable devices, for example, with reverse-facing photodetectors to observe the pupils or with accelerometers to tack the movement of the eyes. Neuromuscular sensors may also be utilized. By monitoring the six muscles that control eye movement, the precise direction of gaze may be determined. A memory element to store prior position and/or acceleration may be required in addition to a position computation system considering present and past sensor inputs. In addition, the system illustrated in FIGS. 15A and 15B are equally applicable to the gaze and tracking system of the present invention. The system is preferably programmed to account for gazing geometries in three-dimensional space.

It is known in the art of optometry that the eyes do not remain completely stable when gazing at a stationary object. Rather, the eyes quickly move back and forth. A suitable system for detecting gaze position would include the necessary filtering and/or compensation to account for visual physiology. For example, such a system may include a low-pass filter or an algorithm specially tuned to a user's natural eye behaviors.

In one exemplary embodiment, the electronics and electronic interconnections are made in the peripheral zone of a contact lens rather than in the optic zone. In accordance with an alternate exemplary embodiment, it is important to note that the positioning of the electronics need not be limited to the peripheral zone of the contact lens. All of the electronic components described herein may be fabricated utilizing thin-film technology and/or transparent materials. If these technologies are utilized, the electronic components may be placed in any suitable location as long as they are compatible with the optics.

The activities of the acquisition sampling signal processing block and system controller (1504 and 1506 in FIG. 15B, respectively) depend on the available sensor inputs, the environment, and user reactions. The inputs, reactions, and decision thresholds may be determined from one or more of ophthalmic research, pre-programming, training, and adaptive/learning algorithms. For example, the general characteristics of eye movement may be well-documented in literature, applicable to a broad population of users, and pre-programmed into system controller. However, an individual's deviations from the general expected response may be recorded in a training session or part of an adaptive/learning algorithm which continues to refine the response in operation of the electronic ophthalmic device. In one exemplary embodiment, the user may train the device by activating a handheld fob, which communicates with the device, when the user desires near focus. A learning algorithm in the device may then reference sensor inputs in memory before and after the fob signal to refine internal decision algorithms. This training period could last for one day, after which the device would operate autonomously with only sensor inputs and not require the fob.

An intraocular lens or IOL is a lens that is implanted in the eye and replaces the crystalline lens. It may be utilized for individuals with cataracts or simply to treat various refractive errors. An IOL typically comprises a small plastic lens with plastic side struts called haptics to hold the lens in position within the capsular bag in the eye. Any of the electronics and/or components described herein may be incorporated into IOLs in a manner similar to that of contact lenses.

Although shown and described in what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A powered ophthalmic lens, the powered ophthalmic lens comprising:
   a contact lens including an optic zone and a peripheral zone; and
   an eye gaze tracking system incorporated into the peripheral zone of the contact lens, the eye gaze tracking system including a sensor to determine and track eye position, a signal conditioning circuit, including a filter to compensate for visual physiology for a particular user's eye, the filter including at least one of hardware or software tuned to a user's natural eye behavior and including an adaptive algorithm for continually refining the eye gaze operation of the ophthalmic lens, a system controller cooperatively associated with the sensor, the system controller configured to determine and track gaze direction in spatial coordinates based on information from the sensor that has passed through the signal conditioning circuit and output a control signal, and at least one actuator configured to receive the output control signal and implement a predetermined function based on a signal from the system controller to change the state of the contact lens, the output control signal being a function of the filtered signal from the sensor.

2. The powered ophthalmic lens according to claim 1, wherein the sensor comprises at least one photodetector positioned to capture an image of the eye.

3. The powered ophthalmic lens according to claim 2, wherein the at least one photodetector comprises a rear-facing camera configured to detect changes in images, patterns, or contrast to track eye movement.

4. The powered ophthalmic lens according to claim 1, wherein the sensor comprises at least one accelerometer to track movement of at least one of the eye or the contact lens.

5. The powered ophthalmic lens according to claim 1, wherein the sensor comprises at least one neuromuscular sensor configured to detect neuromuscular activity associated with eye movement.

6. The powered ophthalmic lens according to claim 1, wherein the eye gaze tracking system further comprises a signal processor configured to receive signals from the sensor, perform digital signal processing, and output one or more signals to the system controller.

7. The powered ophthalmic lens according to claim 6, wherein signal processor comprises associated memory.

8. The powered ophthalmic lens according to claim 1, wherein the eye gaze tracking system further comprises a power supply.

9. The powered ophthalmic lens according to claim 1, wherein the eye gaze tracking system further comprises a communication system for communication with at least a second contact lens.

10. The powered ophthalmic lens according to claim 1, wherein the spatial coordinates are in two dimensions.

11. The powered ophthalmic lens according to claim 1, wherein the spatial coordinates are in three dimensions.

12. The powered ophthalmic lens according to claim 1, wherein the eye gaze tracking system wirelessly interfaces with an external device.

13. A powered ophthalmic lens, the powered ophthalmic lens comprising:
   a contact lens; and
   an eye gaze tracking system incorporated into the contact lens, the eye gaze tracking system including a sensor to determine and track eye position, a signal conditioning circuit, including a filter to compensate for visual physiology for a particular user's eye, the filter including at least one of hardware or software tuned to a user's natural eye behavior and including an adaptive algorithm for continually refining the eye gaze operation of the ophthalmic lens, a system controller cooperatively associated with the sensor, the system controller configured to determine and track gaze direction in spatial coordinates based on information from the sensor that has passed through the signal conditioning circuit and output a control signal, and at least one actuator configured to receive the output control signal and implement a predetermined function based on a signal from the system controller to change the state of the contact lens, the output control signal being a function of the filtered signal from the sensor.

14. The powered ophthalmic lens according to claim 13, wherein the sensor comprises at least one photodetector positioned to capture an image of the eye.

15. The powered ophthalmic lens according to claim 14, wherein the at least one photodetector comprises a rear-facing camera configured to detect changes in images, patterns, or contrast to track eye movement.

16. The powered ophthalmic lens according to claim 13, wherein the sensor comprises at least one accelerometer to track movement of at least one of the eye or the contact lens.

17. The powered ophthalmic lens according to claim 13, wherein the sensor comprises at least one neuromuscular sensor configured to detect neuromuscular activity associated with eye movement.

18. The powered ophthalmic lens according to claim 13, wherein the eye gaze tracking system further comprises a signal processor configured to receive signals from the sensor, perform digital signal processing, and output one or more signals to the system controller.

19. The powered ophthalmic lens according to claim 18, wherein signal processor comprises associated memory.

20. The powered ophthalmic lens according to claim 13, wherein the eye gaze tracking system further comprises a power supply.

21. The powered ophthalmic lens according to claim 13, wherein the eye gaze tracking system further comprises a communication system for communication with at least a second contact lens.

22. The powered ophthalmic lens according to claim 13, wherein the spatial coordinates are in two dimensions.

23. The powered ophthalmic lens according to claim 13, wherein the spatial coordinates are in three dimensions.

24. The powered ophthalmic lens according to claim 13, wherein the eye gaze tracking system wirelessly interfaces with an external device.

25. A powered ophthalmic lens, the powered ophthalmic lens comprising:
   intraocular lens; and
   an eye gaze tracking system incorporated into the intraocular lens, the eye gaze tracking system including a sensor to determine and track eye position, a signal conditioning circuit, including a filter to compensate for visual physiology for a particular user's eye, the filter including at least one of hardware or software tuned to a user's natural eye behavior and including an adaptive algorithm for continually refining the eye gaze operation of the ophthalmic lens, a system controller cooperatively associated with the sensor, the system controller configured to determine and track gaze direction in spatial coordinates based on information from the sensor that has passed through the signal conditioning circuit and output a control signal, and at least one actuator configured to receive the output control signal and implement a predetermined function based on a signal from the system controller to change the start of the intraocular lens, the output control signal being a function of the filtered signal from the sensor.

* * * * *